United States Patent
Harney

(10) Patent No.: US 7,485,426 B2
(45) Date of Patent: Feb. 3, 2009

(54) METHOD AND KITS FOR PREPARING MULTICOMPONENT NUCLEIC ACID CONSTRUCTS

(75) Inventor: Peter D. Harney, Aliso Viejo, CA (US); Jennifer Harney, legal representative, Aliso Viejo, CA (US)

(73) Assignee: Vectorobjects, LLC, Wellesley, MA (US)

( * ) Notice: Subject to any disclaimer, the term of this patent is extended or adjusted under 35 U.S.C. 154(b) by 0 days.

(21) Appl. No.: 11/607,812

(22) Filed: Nov. 30, 2006

(65) Prior Publication Data

US 2008/0032399 A1 Feb. 7, 2008

Related U.S. Application Data

(63) Continuation of application No. 10/280,261, filed on Oct. 24, 2002, now Pat. No. 7,223,539, which is a continuation of application No. 09/220,398, filed on Dec. 24, 1998, now Pat. No. 6,495,318, which is a continuation-in-part of application No. 08/877,034, filed on Jun. 16, 1997, now Pat. No. 6,277,632.

(60) Provisional application No. 60/019,869, filed on Jun. 17, 1996.

(51) Int. Cl.
*C12Q 1/68* (2006.01)
*C07H 21/00* (2006.01)
*C07H 21/02* (2006.01)
*G01N 33/53* (2006.01)
*C12N 1/00* (2006.01)
*C12N 15/00* (2006.01)

(52) U.S. Cl. .............. 435/6; 435/7.1; 435/7.2; 435/91.1; 435/91.2; 435/254.2; 435/320.1; 536/22.1; 536/24.3; 536/24.33; 536/25.3

(58) Field of Classification Search .................. 435/6, 435/7.1, 7.2, 91.1, 91.2, 254.2, 320.1; 536/22.1, 536/24.3, 24.33, 25.3
See application file for complete search history.

(56) References Cited

U.S. PATENT DOCUMENTS

| | | | |
|---|---|---|---|
| 4,987,073 A | 1/1991 | Berman et al. |
| 5,128,256 A | 7/1992 | Huse et al. |
| 5,137,814 A | 8/1992 | Rashtchian et al. |
| 5,426,039 A | 6/1995 | Wallace et al. |

(Continued)

OTHER PUBLICATIONS

Aslanidis and de Jong, Ligation-independent cloning of PCR products (LIC-PCR), *Nucleic Acids Research*, 18(20):6069-6074 (1990).

(Continued)

*Primary Examiner*—Jezia Riley
(74) *Attorney, Agent, or Firm*—Ropes & Gray LLP

(57) ABSTRACT

The invention provides a highly efficient, rapid, and cost effective method of linking nucleic acid components in a predetermined order to produce a nucleic acid multicomponent construct. The invention further provides nucleic acid components, each nucleic acid component comprising a double stranded nucleic acid molecule having at least one single stranded 5' or 3' terminal sequence, the terminal sequence having sufficient complementarity to either a terminal sequence in a separate nucleic acid component or to a sequence in a linking nucleic acid molecule so as to allow for specific annealing of complementary sequences and linkage of the components in a predetermined order. Kits containing reagents required to practice the method of the invention are also provided.

19 Claims, 5 Drawing Sheets

U.S. PATENT DOCUMENTS 5,470,955 A  11/1995  Craig
5,962,255 A  10/1999  Griffiths et al.
6,495,318 B2 * 12/2002  Harney .......................... 435/6

OTHER PUBLICATIONS

Belev et al., "A Fully MOdular Vector System for the Optimization of Gene Expression in *Escherichia coli*," *Plasmid*, 2:147-150 (1991).

Brosius, J., "Laboratory Methods Superpolylinkers in Cloning and Expression Vectors," *DNA*, 8(10):759-777 (1989).

Clark, J.M., "Novel non-templated nucleotide addition reactions catalyzed by procaryotic and eucaryotic DNA polymerases," Laboratory of Molecular Genetics, National Institute of Environmental Health Sciences, Research Triangle Park, NC, *Nucleic Acid Research*, 16(20):9677-9685.

Denis and Brzezinski, "A versatile shuttle consmid vector for use in *Escherichia coli* and actinomycetes," *Gene*, 111:115-118 (1992).

Gibson et al., "Loristo, a cosmid vector with BamHI, NotI, ScaI and HindIII cloning sites and altered neomycin phosphotransferase gene expression," *Gene*, 53:283-286 (1987).

Goeddel et al., "Gene Expression Technology," *Method in Enzymology*, 185:512-527 (1992).

Goodchild, *Bioconjugate Chemistry*, 1(3):165-187.

Marchuk et al., "Construction of T-vectors, a rapid and general system for direct cloning of unmodified PCR products," *Nucleic Acids Research*, 19(5):1154 (1990).

MacNeil et al., "Analysis of Streptomyces avermitilis genes required for avermectin biosynthesis utilizing a novel integration vector," *Gene*, 111:61-68 (1992).

Scharf et al., "Direct Cloning and Sequence Analysis of Enzymatically Amplified Genomic Sequences," *Science*, 233(4768):1076-1078 (1986).

Watson et al., "Recombinant DNA, Second Edition," (1994).

* cited by examiner

NON-PALINDROMIC COMPATIBLE OVERHANGS

5' COMPATIBLE OVERHANGS

3' COMPATIBLE OVERHANGS

BRIDGE COMPATIBLE WITH 3' AND 5' OVERHANGS

ADAPTOR COMPATIBLE 3' OVERHANGS

SEQUENCE LISTING

```
<160> NUMBER OF SEQ ID NOS: 16

<210> SEQ ID NO 1
<211> LENGTH: 15
<212> TYPE: DNA
<213> ORGANISM: Artificial Sequence
<220> FEATURE:
<223> OTHER INFORMATION: non-palindronic complementary terminal sequence

<400> SEQUENCE: 1
atgctatggc atact                                                    15

<210> SEQ ID NO 2
<211> LENGTH: 15
<212> TYPE: DNA
<213> ORGANISM: Artificial Sequence
<220> FEATURE:
<223> OTHER INFORMATION: non-palindronic complementary terminal sequence

<400> SEQUENCE: 2
agtatgccat agcat                                                    15

<210> SEQ ID NO 3
<211> LENGTH: 35
<212> TYPE: DNA
<213> ORGANISM: Artificial Sequence
<220> FEATURE:
<223> OTHER INFORMATION: primer
```

<400> SEQUENCE: 3
gggaattcat ggactggacc tggaggrtcy tctkc                              35

<210> SEQ ID NO 4
<211> LENGTH: 34
<212> TYPE: DNA
<213> ORGANISM: Artificial Sequence
<220> FEATURE:
<223> OTHER INFORMATION: primer

<400> SEQUENCE: 4
gggaattcat ggagyttggg ctgasctggs tttt                               34

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
gggaattcat grammwactk tgkwscwysc tyctg                              35

<210> SEQ ID NO 6
<211> LENGTH: 35
<212> TYPE: DNA
<213> ORGANISM: Artificial Sequence
<220> FEATURE:
<223> OTHER INFORMATION: primer

<400> SEQUENCE: 6
gggaattcat ggacatgrrr dycchvgykc asctt                              35

<210> SEQ ID NO 7
<211> LENGTH: 35
<212> TYPE: DNA
<213> ORGANISM: Artificial Sequence
<220> FEATURE:
<223> OTHER INFORMATION: primer

<400> SEQUENCE: 7
gggaattcat grcctgswcy cctctcytyc tswyc                              35

<210> SEQ ID NO 8
<211> LENGTH: 28
<212> TYPE: DNA
<213> ORGANISM: Artificial Sequence
<220> FEATURE:
<223> OTHER INFORMATION: primer

<400> SEQUENCE: 8
ccaagcttag acgaggggga aaagggtt                                      28

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
ccaagcttgg aggagggtgc caggggg                                       27

<210> SEQ ID NO 10

<211> LENGTH: 27
<212> TYPE: DNA
<213> ORGANISM: Artificial Sequence
<220> FEATURE:
<223> OTHER INFORMATION: primer

<400> SEQUENCE: 10
ccaagcttga agctcctcag aggaggg        27

<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
ccaagctttc atcagatggc gggaagat       28

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
ggggaattca tgrasttskg gytmarctkg rtt      33

<210> SEQ ID NO 13
<211> LENGTH: 34
<212> TYPE: DNA
<213> ORGANISM: Artificial Sequence
<220> FEATURE:
<223> OTHER INFORMATION: primer

<400> SEQUENCE: 13
ggggaattca tgraatgsas ctgggtywty ctct     34

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
ggggaattcs aggtgmagct cswrsarycs ggg      33

<210> SEQ ID NO 15
<211> LENGTH: 38
<212> TYPE: DNA
<213> ORGANISM: Artificial Sequence
<220> FEATURE:
<223> OTHER INFORMATION: primer

<400> SEQUENCE: 15
ggaagcttay ctccacacac aggrrccagt ggatagac   38

<210> SEQ ID NO 16
<211> LENGTH: 29
<212> TYPE: DNA
<213> ORGANISM: Artificial Sequence
<220> FEATURE:
<223> OTHER INFORMATION: primer

```
<400> SEQUENCE: 16
ggaagcttac tggatggtgg gaagatgga                                        29
```

METHOD AND KITS FOR PREPARING MULTICOMPONENT NUCLEIC ACID CONSTRUCTS

RELATED APPLICATIONS

This application is a continuation of U.S. application Ser. No. 10/280,261, filed Oct. 24, 2002, now U.S. Pat. No. 7,223, 539 which is a continuation of U.S. Ser. No. 09/220,398, filed Dec. 24, 1998, now U.S. Pat. No. 6,495,318 which is a continuation-in-part of U.S. Ser. No. 08/877,034, filed Jun. 16, 1997, now U.S. Pat. No. 6,277,632 which claims the benefit of a previously filed Provisional Application No. 60/019,869 filed Jun. 17, 1996, the specifications of which are hereby incorporated by reference.

BACKGROUND OF THE INVENTION

The essence of recombinant DNA technology is the joining of two or more separate segments of DNA to generate a single DNA molecule that is capable of autonomous replication in a given host. The simplest constructions of hybrid DNA molecules involve the cloning of a DNA sequence of interest (such as DNA insert containing a natural or synthetic gene or gene fragment) into a pre-assembled cloning vector. The cloning vector includes all of the necessary components for replication of the DNA insert in a compatible host cell, e.g., promoter sequence, origin of replication sequence, termination sequence, and a selectable marker sequence. The DNA insert sequences can be derived from essentially any organism, and they may be isolated directly from the genome, from mRNA, or from previously cloned DNA sequences. Alternatively, the DNA insert sequences can be created synthetically.

Insertion of the DNA sequence of interest can be accomplished by a number of techniques. The most common technique involves restriction enzymes. A restriction enzyme recognition site that is present in both the DNA insert and the vector of interest is cleaved with a restriction enzyme to provide for appropriate termini, the termini of either the DNA insert or the vector are treated with alkaline phosphatase to remove terminal phosphates and avoid undesirable joining, and the DNA sequence of interest is inserted into the vector at the compatible sites during a ligation reaction. A restriction enzyme site present in a pre-assembled vector must be compatible with a restriction enzyme site in the DNA sequence of interest.

Alternatively, the DNA of interest can be modified to obtain compatible restriction sites by filling in of cohesive ends as appropriate, or by the ligation of an appropriate oligonucleotide linker, which can be subsequently cleaved by the restriction enzyme of interest.

Conventional cloning methods can be time consuming and often involve multiple sub cloning steps. Therefore, a need exists for developing a simple and rapid method for synthesizing and identifying an optimal construct for use in a particular application.

SUMMARY OF THE INVENTION

This invention pertains to methods for preparing multicomponent nucleic acid constructs. The method of the invention has a wide variety of applications for the expression of synthetic and naturally occurring genes or gene fragments. The invention provides integral vector elements which may be specifically selected or which may varied so as to create a collection of vectors from which optimal configurations can be selected or screened for. These integral vector elements include both vector backbone elements, which do not directly affect the expression or form of the insert gene or gene fragment, and insert modifying vector elements which alter the expression and/or form of the insert-encoded gene product. This system for the rapid and flexible assembly of specific multicomponent nucleic acid constructs is referred to as GEOS (for Genetic Engineering Operating System). GEOS methodology has numerous applications ranging from the assembly of simple circular expression vectors to the production of complex linar assemblies which function as small chromosomes. Various applications of GEOS methodology are discussed in detail below and still others will be apparent to the skilled artisan.

The invention further provides a method of linking the vector element nucleic acid components in a predetermined order so as to produce a nucleic acid multicomponent construct.

In certain preferred embodiments, the GEOS method comprises:

(a) providing the nucleic acid components to be assembled into the construct, each nucleic acid component comprising a double stranded nucleic acid molecule having at least one single stranded 5' or 3' terminal sequence, the terminal sequence having sufficient complementarity to a terminal sequence in a separate nucleic acid component so as to allow for specific annealing of complementary sequences and linkage of the components in a predetermined order;

(b) incubating the nucleic acid components under conditions which allow for the specific annealing and linkage of the nucleic acid components to thereby produce the nucleic acid multicomponent construct.

In another preferred embodiments, the GEOS method comprises:

(a) providing the nucleic acid components and one or more linking nucleic acid molecules to be assembled into the construct, each nucleic acid component comprising a double stranded nucleic acid molecule having at least one single stranded 5' or 3' terminal sequence, the terminal sequence having sufficient complementarity to a sequence in a linking nucleic acid molecule so as to allow for specific annealing of complementary sequences and linkage of the components in a predetermined order;

(b) incubating the nucleic acid components under conditions which allow for the specific annealing and linkage of the nucleic acid components to thereby produce the nucleic acid multicomponent construct.

The genetic element portion(s) of the nucleic acid components can be double- or single-stranded, though are preferably double-stranded.

In a preferred embodiment of the method, the nucleic acid components are flanked by single stranded terminal sequences and these terminal sequences are preferably non-palindromic. The nucleic acid components can be linked either directly via annealing of 5' or 3' complementary terminal sequences or indirectly via a linking nucleic acid molecule (e.g. an oligonucleotide or an adaptor molecule).

The nucleic acid components can be linked either simultaneously or sequentially to form the nucleic acid construct. Sequential assembly is suitable for automation. The method can be used to produce nucleic acid constructs which are functional as assembled or constructs which are used as subcomponents for the assembly of functional constructs.

The method of the invention can be used to synthesize a group of nucleic acid constructs in which one or more of the components can be substituted, in each of the constructs, with a different nucleic acid component, having the same functionality or characteristic utility. This allows for comparison of the different components and production of an optimal construct for a particular application. Toward this end, the nucleic acid components are designed and synthesized in such a way that a group of nucleic acid components belonging in the same category (i.e., having the same functionality or characteristic utility, e.g. a set of nucleic acid components encoding different promoters) possess the same terminal sequences, such that the same category nucleic acid components can be used interchangeably to assemble a nucleic acid multicomponent construct.

The nucleic acid components may also be covalently or non-covalently modified prior to or following assembly of the nucleic acid multicomponent construct. This allows for the synthesis of constructs having biological properties which cannot be obtained easily using current recombinant methods. For instance, the modification utilizes an arylboronic acid reagent, such as phenyldiboronic acid.

The method of this invention is particularly suitable for the construction of nucleic acid vectors. These include plasmid, viral, or phage vectors, or yeast artificial chromosomes. The vector can be a cloning or expression vector and can be used for the expression of cDNA or genomic libraries, genes or gene fragments, mutagenized genes, recombined fusion genes, and artificial genes. The constructs can be employed in prokaryotic, eukaryotic (mammalian or non-mammalian) expression, construction of unique cDNA libraries, protein, antibody and peptide phage display libraries. The constructs can further be employed in gene transfer, gene therapy, and the creation of transgenic organisms.

According to the method, the vector is assembled from nucleic acid components encoding a single functionality or multiple functionalities. In some applications of the invention, more than one biological function may be bundled into a single nucleic acid component. This may be desirable when, for example, one seeks to limit the overall number of components to be assembled into the GEOS construct. In one embodiment of the invention, nucleic acid components encoding an origin of replication, a selectable marker and an insert of interest are used. Depending on the type of vector desired, nucleic acid components encoding other vector functions may also be incorporated (e.g. a promoter, a transcription or translation regulatory element, etc.). An expression vector can be produced using a nucleic acid component encoding a structural gene or gene fragment of interest and additional nucleic acid components encoding regulatory elements required for expression of the gene. For example, a cDNA library expression vector is produced using nucleic acid components encoding a collection of cDNA molecules derived from poly(A)+ mRNA. Importantly, the optimization procedure of interchanging nucleic acid components described above can be used to create an optimal vector for a particular application.

The invention further provides a kit for the production of vectors. In one embodiments, the kit for the production of vectors would minimally comprise nucleic acid components encoding origins of replication and selectable markers and optionally, transcriptional regulatory sequence(s). The kit could also include nucleic acid components encoding other vector functions (e.g. a promoter, a transcription or translation regulatory element, etc.).

The invention further provides a kit for the production of vectors. The kit for the production of vectors would minimally comprise nucleic acid components encoding origins of replication, selectable markers and inserts of interest. The kit could also include nucleic acid components encoding other vector functions (e.g. a promoter, a transcription or translation regulatory element, etc.).

The method of the invention is a highly efficient, rapid, cost effective alternative to current recombinant cloning methods in that it enables users to choose from a broad array of different nucleic acid components or modified nucleic acid components when assembling any construct. The method of the invention allows the rapid construction of customized constructs without the need to use restriction enzymes.

Other features and advantages of the invention will be apparent from the following detailed description, and from the claims.

BRIEF DESCRIPTION OF THE DRAWINGS

FIG. 2 shows representative ways of linking nucleic acid components via specific terminal sequences to prepare nucleic acid constructs according to the method of the invention.

DETAILED DESCRIPTION OF THE INVENTION

I. Overview

Figure 1:
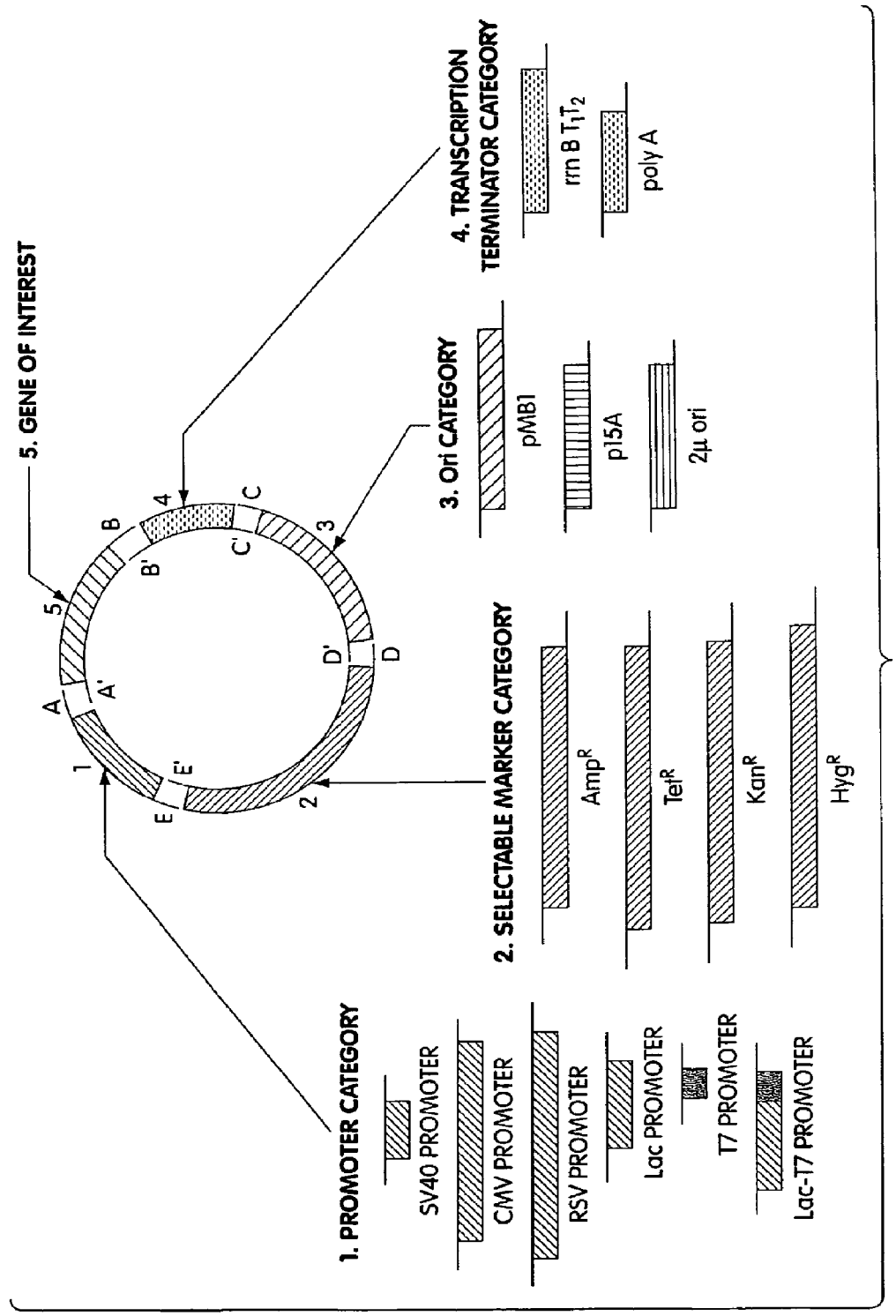
FIG. 1 is a schematic representation of the assembly of a circular plasmid, using the method of the invention. The plasmid vector is assembled by combining a set of nucleic acid components which possess complementary terminal sequences, as well as all of the necessary genetic elements required to generate a functional plasmid construct. A partial list of different interchangeable nucleic acid components and their respective categories is shown, demonstrating the flexibility and utility of the method of the invention.

One of the most powerful techniques in molecular biology involves the use of restriction enzymes for the purpose of cloning DNA inserts into a specific site in a cloning vector. However, as described herein, the use of restriction-based cloning techniques has certain limitations, particularly with regard to generation of multicomponent combinatorial libraries. The invention described herein enables the rapid and precise generation of a wide range of nucleic acid constructs, including highly optimized vectors containing cloned inserts, without the use of restriction enzymes and without prior knowledge of the sequence of the cloned insert.

The present method is based on the ability to assemble a multitude of individual nucleic acid components, including genes, gene fragments and other genetic elements, into a useful nucleic acid construct such as a vector. The invention further provides a method for nucleic acid components in a predetermined order to produce a nucleic acid construct. Components incorporate unique and specifiable terminal sequences, or overhangs, which are preferably non-palindromic and single stranded, and which serve to direct the site-specific localization of each component within an assembled construct, such that one overhang, A, will anneal preferably with a discrete, complementary overhang, A', located on an adjacent component. Several alternative methods for joining adjacent components are described in FIG. 2, including those that might also utilize oligonucleotide bridges and adaptor molecules.

Categories of components having the same functionality, or characteristic utility, can be designed and synthesized to incorporate the same overhangs, thereby enabling the interchangeable deployment of components from a specific category. According to the method, the construct is assembled from nucleic acid components encoding a single functionality or multiple functionalities. In some applications of the invention, more than one functionality may be bundled into a single nucleic acid component especially when, for example, one wishes to limit the overall number of components to be assembled into the construct. As described herein, the present invention provides a method for creating combinatorial arrays of constructs from a limited set of nucleic acid components.

In one embodiment of this method, the generation of a wide array of candidate DNA vaccine constructs is greatly simplified. When specifically applied to somatic gene immunization, the current method enables the rapid assembly and systematic variation of critical components, including a general component for the expression vector backbone, components corresponding to framework regions, components corresponding to complementarity-determining regions (CDRs), components corresponding to tissue-specific immunoglobulin promoter and/or enhancer elements, and one or more antigenic epitope components to be inserted into any one or more of the CDR domains.

Novel genes and gene products can also be generated utilizing this invention. In one embodiment, a library of antibodies can be displayed on the surface of a lambda phage by selecting individual components from a category of cDNA components representative of an antibody framework region, a category of cDNA components representative of a hypervariable region, and one or more user-definable components which incorporate user-specifiable genetic elements required to express antibody fusions on the surface of the phage.

Other aspects of the invention show that components may be covalently modified or altered prior to assembly, and following assembly, constructs would incorporate one or more of these modifications. These modifications may act as the site of attachment for small biological molecules or macromolecular biological molecules, including proteins and carbohydrates. The ease and flexibility of modification to components rather than constructs may improve the specificity of many gene therapy vectors, especially those requiring import into the nucleus in order for expression to occur. In one embodiment, the design of candidate vector therapeutic constructs would involve the deployment of a multitude of user-definable vector components, resulting in the generation of a combinatorial array of vectors. A discrete category of components to facilitate nuclear targeting, able to be covalently modified using an array of cationic peptides, could then be assembled with other components into an exquisitely specifiable construct.

In another embodiment, covalent modification of a component using methods know in the art can result in the reversible but stable attachment of that component to a solid phase. In such an example, the subsequent stepwise addition of components containing compatible overhangs would result in a uniquely automatable process for assembling arrays of vectors or other constructs.

In another embodiment, both viral and phage genomes, as well as vector constructs, may utilize altered or mutagenized components. Such components would enable the mutation or deletion of one or more genes, the enhancement of specific gene functions, the construction of fusion genes, or, for instance, the addition or deletion of restriction enzyme sites.

In a particularly preferred embodiment of the invention, individual components comprise exonic and intronic units which can used to facilitate rearrangement of discrete polypeptide-encoding exon units. The invention thereby facilitates the formation of peptide domain "shuffled" libraries encoded by exonic units which are linked by intronic units. Thus the invention can be readily applied to the creation of unique proteins peptide domain shuffling and in vitro selection techniques. In one particular embodiment of the peptide domain shuffling application a pool of diverse peptide domain-encoding nucleic acid components is added to a construct assemblage. A compatible intronic unit is then added prior to the addition of another pool of diverse peptide domain-encoding exonic nucleic acid components. The resulting assembly increases in heterogeneity with successive addition of peptide domain-encoding components and provides a convenient source of diversity for subsequent screening or selection processes. This methodology thereby enables the user to create synthetically "evolved" proteins comprised of discrete polypeptide domains which have been randomized and infinitely "shuffled."

The invention further provides a kit for the production of vectors. In one embodiments, the kit for the production of vectors would minimally comprise nucleic acid components encoding origins of replication and selectable markers and optionally, transcriptional regulatory sequence(s). The kit could also include nucleic acid components encoding other vector functions (e.g. a promoter, a transcription or translation regulatory element, etc.).

The invention further provides a kit for the production of vectors. The kit for the production of vectors would minimally comprise nucleic acid components encoding origins of replication, selectable markers and inserts of interest. The kit could also include nucleic acid components encoding other vector functions (e.g. a promoter, a transcription or translation regulatory element, etc.).

II. Definitions

In order that the invention may be more readily understood, certain terms are first defined.

As used herein, the term "GEOS" stands for Genetic Engineering Operating System and is meant to refer to the generalized method of the immediate invention which employs both a flexible strategy for vector assembly from selected nucleic acid components encoding various biological functions, and which further employs methods for the rapid chemical joining of these selected nucleic acid components to create expression vectors which are ideally suited to a particular purpose.

As used herein, the term "vector" is intended to include both circular and linear assemblies of nucleic acid components. Examples of linear vectors include various viral genomes as well as yeast artificial chromosomes (YACs) and mammalian artificial chromosomes (see e.g. Grimes and Cooke (1998) Hum Mol Genet, 7: 1635-40; Vos (1998) Curr Opin Genet Dev, 8: 351-9).

The terms "nucleic acid component", "vector component" and "vector element", which used interchangeably herein, describe the basic unit of assembly used in the present invention. These units are comprised of nucleic acid molecules, preferably double stranded, which contain at their termini specific terminal sequences required for assembling the nucleic acid components into a specific nucleic acid multi-component construct. The nucleic acid sequences contained within each nucleic acid component provide the requisite information for a specific biological function or functions or for a specific utility deemed essential by the user. Examples of nucleic acid components include nucleic acid sequences which encode a polypeptide, include an origin of replication, and/or include a selectable marker, alone or in combination with other biologically active nucleotide sequences.

The term "nucleic acid" refers to polynucleotides such as deoxyribonucleic acid (DNA), and, where appropriate, ribonucleic acid (RNA). The term should also be understood to include, as equivalents, analogs of either RNA or DNA.

As used herein, the term "terminal sequence" is used to describe the terminal single stranded nucleotide sequence of a nucleic acid component. Nucleic acid components having complementary terminal sequences to either separate nucleic acid components or linking molecules enable users to specify the precise organization and orientation of nucleic acid components upon their assembly into constructs.

The terms "complementary" and "compatible" are used herein interchangeably to describe the capacity of a pair of single-stranded terminal sequences to anneal to each other via base pairing (e.g. A-T or G-C). The terminal sequences should contain nucleotide sequences of sufficient length and sequence complementarity so as to allow efficient annealing to occur.

As used herein, the term "palindromic sequence", which is art recognized, describes a sequence of DNA that consists of inverted repeats.

As used herein, the term "linkage" refers to a physical connection, preferably covalent coupling, between two or more nucleic acid components, e.g., catalyzed by an enzyme such as a ligase.

As used herein, the term "genomic library" refers to a set of cloned fragments together representing the entire genome of an organism.

As used herein, the term "category" describes a classification of genes, gene fragments, restriction sites, or other genetic elements found in the subject nucleic acid components which may be arranged in a systematic order based on a number of user-defined criteria, including the ability to produce or regulate a similar biological activity. For example, the various different origin of replication nucleotide sequences, may be classified as a specific category. Marker genes, transcriptional regulatory sequence and the like are each other examples of categories of functionality which be provide in the nucleic acid components.

As used herein, the term "hapten" refers to a small molecule that acts as an antigen when conjugated to a protein.

As used herein, the term "genetic element" describes a sequence of nucleotides, including those which encode a regulatory region, involved in modulating or producing biological activity or responses or which provides a specific signal involved in a molecular mechanism or biological activity. For example, a prokaryotic gene may be comprised of several genetic elements, including a promoter, a protein coding region, a Shine-Delgarno sequence, and translational and transcriptional terminators.

As used herein, the term "functionality" describes the normal, characteristic utility or utilities of a construct, gene, gene fragment, or genetic element.

As used herein, the term "handle" is used to describe a chemical or biochemical modification to a nucleotide residue within an oligonucleotide or a nucleic acid component. A handle provides a site for covalent or non-covalent attachment of a biological or chemical molecule(s) to a nucleic acid component.

As used herein, the term "oligonucleotide" refers to a single stranded nucleic acid sequence composed of two or more nucleotides. An oligonucleotide can be derived from natural sources, but it is often chemically synthesized by known methods and then purified. It may be of any length and it may be used as a primer, a probe or a component of a ligation reaction.

As used herein, the term "oligonucleotide bridge" is an oligonucleotide used in a ligation reaction to bridge non-complementary 5' and 3' terminal sequences in two separate nucleic acid components.

As used herein, the term "semi-cruciform" refers to a pair of partially complementary oligonucleotides which, when annealed together, function as an oligonucleotide bridge to bring together non-complementary 5' and 3' terminal sequences in two separate nucleic acid components. The two oligonucleotides comprising the bridge include one which carries, at its 5' end, a sequence which is complementary to the 5' overhang of one of the nucleic acid components and another oligonucleotide which carries, at its 3' end, a sequence which is complementary to the 3' overhand of the other nucleic acid component.

As used herein, the term "promoter" refers to a DNA sequence which is recognized by an RNA polymerase and which directs initiation of transcription at a nearby downstream site. As used herein "promoter" refers to viral, prokaryotic or eukaryotic transcriptional control sequences.

As used herein, the term "enhancer" refers to a DNA sequence which, without regard to its position or its orientation in the DNA, increases the amount of RNA synthesized from an associated promoter. Enhancers are typically found in association with eukaryotic or viral promoters and frequently confer tissue-specific and/or developmental-specific expression of the linked promoter.

As used herein, the term "silencer" refers to a DNA sequence which, without regard to its position or its orientation in the DNA, decreases the amount of RNA synthesized from an associated promoter. Silencers are typically found in association with eukaryotic promoters and frequently confer tissue-specific and/or developmental-specific expression of the linked promoter.

As used herein, the term "transcriptional terminator" refers to a DNA sequence which promotes the formation of a 3' end of an RNA transcript. As used herein the term "transcriptional terminator" refers to viral, prokaryotic or eukaryotic transcriptional terminator sequences (e.g. polyadenylation signal sequences).

As used herein, the term "origin of replication" refers to a DNA sequence which promotes the initiation of DNA synthesis by a DNA polymerase. As used herein the term refers to viral, prokaryotic or a eukaryotic replication origins.

As used herein, the term "exon" refers to a segment of DNA which encodes a portion of a mature RNA transcript.

As used herein, the term "intron" refers to a segment of DNA which encodes a portion of a primary transcript that is not included in a mature RNA transcript. As used herein, the term intron is interchangeable with the term "intervening sequence" and generally refers to a portion of a primary transcript, or the corresponding segment of DNA encoding such a portion, which is removed from a mature RNA transcript by splicing processes.

III. Exemplary GEOS Methodology

The GEOS methodology can be divided into two phases. In one phase, the nucleic acid components are selected and in another phase the selected nucleic acid components are chemically joined. These phases are considered separately below, although it will be obvious to a skilled individual that the two phases are interdependent in that selection of particular nucleic acid components will influence the selection of chemical joining methods. We begin with an examination of the various chemical joining methods which can be used in the method of the invention.

A. GEOS Chemical Joining Methods

The present invention pertains to a highly efficient, rapid, and cost effective method of producing multicomponent nucleic acid constructs by means of facile chemical joining techniques. In certain preferred embodiments, the GEOS method comprises:

(a) providing the nucleic acid components to be assembled into the construct, each nucleic acid component comprising a double stranded nucleic acid molecule having at least one single stranded 5' or 3' terminal sequence, the terminal sequence having sufficient complementarity to a terminal sequence in a separate nucleic acid component so as to allow for specific annealing of complementary sequences and linkage of the components in a predetermined order;

(b) incubating the nucleic acid components under conditions which allow for the specific annealing and linkage of the nucleic acid components to thereby produce the nucleic acid multicomponent construct.

In another preferred embodiments, the GEOS method comprises:

(a) providing the nucleic acid components and one or more linking nucleic acid molecules to be assembled into the construct, each nucleic acid component comprising a double stranded nucleic acid molecule having at least one single stranded 5' or 3' terminal sequence, the terminal sequence having sufficient complementarity to a sequence in a linking nucleic acid molecule so as to allow for specific annealing of complementary sequences and linkage of the components in a predetermined order;

(b) incubating the nucleic acid components under conditions which allow for the specific annealing and linkage of the nucleic acid components to thereby produce the nucleic acid multicomponent construct.

In many aspects of its practice, the subject method will be carried out in a combinatorial fashion, e.g., to produce a variegated library of multicomponent constructs. In this regard, if there are N component positions in the final multicomponent construct, and $Y_N$ different nucleic acid components at each position N, then the combinatorial library will include $\{Y_1 \times Y_2 \times \ldots Y_{N-1} \times Y_N\}$ different multicomponent constructs. To further illustrate, for a three component construct, e.g., N=3, if there are 2 different choices of components at two positions and 4 different choices of components at the third position, the combinatorial library can include up to 16 different three component constructs (2×2×4). This point is illustrated further in connection with Table I. In preferred embodiments, N is 3 or greater, more preferably in the range of 3-10, and even more preferably 3-8. Preferably the library includes multicomponent constructs having at least 3 different nucleic acid components, rather than being oligomers of a single component.

When the interactions of the nucleic acid components are random, the order and composition of the resulting constructs of the combinatorial library generated is also random. For instance, where the variegated population of nucleic acid components used to generate the combinatorial genes comprises X different components, random assembly of the components can result in $X^N$ different genes having N component positions. Where 5 different nucleic acid components are used (X=5), the combinatorial approach can give rise to 625 different genes having 4 component positions, and 780 different genes having from 1 to 4 component positions (e.g. from the binomial $$\sum_{1}^{N} X^N, \text{ or } X^1 + X^2 \ldots + X^{N-1} + X^N).$$

It will be appreciated that the frequency of occurrence of a particular component in the combinatorial library may also be influenced by, for example, varying the concentration of that component positions relative to the other component positions present, or altering the flanking overhang sequences of that component to either diminish or enhance its annealing ability relative to the other component positions being admixed.

However, the present GEOS method can also be utilized for ordered gene assembly, and carried out in much the same fashion as automated oligonucleotide or polypeptide synthesis, such as through the use of resin-bound nucleic acid components in the ordered synthesis of a gene.

In a preferred embodiment of the invention, the nucleic acid components are used in an appropriately phosphorylated form for ligation. Typically, the nucleic acid components are incubated at a temperature appropriate to promote denaturation, cooled down to an appropriate temperature, such that efficient annealing of the nucleic acid component terminal sequences occurs, and treated with a ligase enzyme to ligate the nucleic acid components and produce a nucleic acid construct. The formed nucleic acid construct can be transformed into a bacterial host for amplification and subsequent purification.

The method of the present invention entails the use of specially designed nucleic acid components to assemble a nucleic acid construct. In one embodiment, the nucleic acid components are double stranded nucleic acid molecules having one or more, preferably two terminal sequences designed to be complementary to the terminal sequences of the nucleic acid component intended to be the adjacent component in the construct. For example, in a construct containing five components in order 1-5 (see FIG. 1), the terminal sequence E of nucleic acid component 1 would be compatible only with the terminal sequence E', of nucleic acid component 2, the terminal sequence D of nucleic acid component 2 with the terminal sequence D' of nucleic acid component 3, the terminal sequence C of nucleic acid component 3 with the terminal sequence C' of nucleic acid component 4 and the like.

In a preferred embodiment of the method, the nucleic acid components are flanked by single stranded terminal sequences and the terminal sequences of the component are non-palindromic.

The nucleic acid components can be linked either directly via annealing of 5' or 3' complementary terminal sequences or indirectly via a linking nucleic acid molecule, which can be, for example, a) an oligonucleotide bridge having a sequence that is complementary to 5' and 3' terminal sequences in two separate nucleic acid components or b) an adaptor molecule having terminal sequences that are complementary with 5' or 3' terminal sequences in separate nucleic acid components.

Alternatively, the nucleic acid components may be provided in the form of single stranded nucleic acid molecules, which would under the appropriate denaturation and annealing conditions, come together to form a double stranded nucleic acid molecule having at least one single stranded 5' or 3' terminal sequence.

In one embodiment of the method, the nucleic acid components can be linked simultaneously to form the nucleic acid construct. Simultaneous assembly involves the incubation of nucleic acid components required for the assembly of a construct of interest, in the same reaction mixture. In another embodiment of the method, the nucleic acid components can be linked sequentially to form the nucleic acid construct. Sequential assembly is performed in a series of different reaction mixtures. This unique attribute lends itself to the automation of construct assembly. The method of the invention uses, preferably, attachment to a solid support as a starting point in the assembly of a series of nucleic acid components, in a defined order, to form a multicomponent nucleic acid construct. The method can be used to produce nucleic acid constructs which are functional as assembled (e.g. vectors) or constructs which are used as subcomponents for the assembly of functional constructs (e.g. genes or gene fragments attached to regulatory elements required for the expression of the gene or the gene fragment).

In still another embodiment, the method of the invention can be used to synthesize a group of nucleic acid constructs in which one or more of the components is substituted, in each of the constructs, with a different component, having the same functionality or characteristic utility. In this way the function of the different components can be evaluated and an optimal construct for a particular application identified. For example, as Table I shows, a cloning vector comprised of five different categories of nucleic acid components (e.g. origin of replication, resistance gene, promoter, etc.) might be designed so that users could choose amongst 5 different choices of nucleic acid components within each category. The number of permutations, or possible vector combinations, which are achievable from these 5 components is 3,125. Thus, it can be easily shown that a huge variety of different nucleic acid constructs which potentially address a wide range of highly specific user needs can be synthesized using a very small number of nucleic acid components.

TABLE I

Permutation of Constructs

| Number of Different Nucleic Acid | No. of Components within a Category | | | | |
|---|---|---|---|---|---|
| Component Categories | 1 | 2 | 3 | 4 | 5 |
| 1 | 1 | 2 | 3 | 4 | 5 |
| 2 | 2 | 4 | 9 | 16 | 25 |
| 3 | 3 | 8 | 27 | 64 | 125 |
| 4 | 4 | 16 | 81 | 256 | 625 |
| 5 | 5 | 32 | 243 | 1,024 | 3,125 |

In preferred embodiments, the subject method is used to produce a combinatorial nucleic acid library having at least 4 different multicomponent constructs, more preferably at least 8, and even more preferably at least 16.

In another embodiment, the nucleic acid components may be covalently or non-covalently modified prior to or following assembly of the nucleic acid multicomponent construct. For instance, sites for the attachment of small biological molecules or macromolecular biological molecules, including proteins or carbohydrates may be added, enabling users to synthesize constructs having altered biological properties.

The method of this invention is particularly suitable for the construction of nucleic acid vectors. These include plasmid, viral, or phage vectors, or artificial chromosomes, e.g., such as for use in bacteria, yeast or mammalian cells. The vector can be a cloning or expression vector and can be used for the expression of cDNA or genomic libraries, genes or gene fragments, mutagenized genes, recombined fusion genes, and artificial genes. The constructs can be employed in prokaryotic, eukaryotic (mammalian or non-mammalian) expression, construction of unique cDNA libraries, protein, as well as antibody and peptide display libraries (e.g. phage peptide display libraries and mammalian peptide display libraries). The constructs can further be employed in gene transfer, gene therapy, and the creation of transgenic organisms.

According to the method, the vector is assembled from nucleic acid components providing a single functionality or multiple functionalities as appropriate. In one embodiment, a nucleic acid components including an origin of replication, a selectable marker and an insert of interest, such as an open reading frame, are used. Depending on the type of vector desired, nucleic acid components encoding other vector functions may also be incorporated (e.g. a promoter, a transcription or translation regulatory element, etc.). An expression vector can be produced using a nucleic acid component encoding a structural gene or gene fragment of interest and additional nucleic acid components encoding regulatory elements required for expression of the gene. For example, a cDNA library expression vector is produced using nucleic acid components encoding a collection of cDNA molecules derived from poly(A)+ mRNA. Importantly, the optimization procedure of interchanging nucleic acid components described above can be used to create an optimal vector for a particular application.

B. General Methods Used in the Practice of the Invention

The practice of the present invention will employ, unless otherwise indicated, conventional techniques of recombinant DNA, molecular biology, cell biology, cell culture, transgenic biology, microbiology, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989).

i) Nucleic Acid Purification

Nucleic acid isolation procedures are performed essentially as described in Maniatis et al. Common nucleic acid isolation procedures involve cell lysis by detergents, protease treatment, and CsCl gradient purification. The latter step can be alternatively performed using commercially available binding matrices in the form of columns (e.g. Qiagen Kit).

ii) Oligonucleotide Synthesis

Oligonucleotide synthesis from the phosphoramidite versions of the nucleosides that DNA and RNA are composed from may be carried out on commercially available solid phase oligonucleotide synthesis machines (Needham-VanDevanter, D. R., et al., *Nucleic Acids Res.,* 12:6159-6168, 1984), or chemically synthesized using the solid phase phosphoranmidite triester method described by Beaucage et al., (Beaucage et al., *Tetrahedron Letts.* 22, No. 20:1859-1862, 1981).

Oligonucleotides are purified prior to use. Purification of oligonucleotides can be performed using reverse phase or anion-exchange HPLC and may also be carried out by denaturing or native polyacrylamide gel electrophoresis. Following purification, oligonucleotides can be phosphorylated using T4 polynucleotide kinase. As used herein, the term "T4 polynucleotide kinase" refers to the enzyme catalyzing the transfer of the terminal (γ) phosphate of ATP to the 5' OH-terminus of a nucleic acid molecule.

iii) Restriction Enzyme Digestion

The procedures concerning the use of restriction enzymes, their nucleotide specificity and the appropriate reaction conditions are known to those skilled in the art and readily available. The amounts of enzyme and DNA, the buffer and ionic concentrations, and the temperature and duration of the reaction will vary depending upon the specific application as described in Maniatis et al.

iv) Ligation

Ligation of single stranded terminal sequences can be catalyzed by a ligase. As used herein, the term "ligase" refers to an enzyme that is capable of joining the 3' hydroxyl terminus of one nucleic acid molecule to a 5' phosphate terminus of a second nucleic acid molecule to form a single molecule. Most preferably, the T4 DNA ligase is used.

Ligation is carried out at 12° C. to 16° C. to maintain a balance between annealing of the terminal sequences and activity of the enzyme. An appropriate buffer containing the ATP cofactor required by the ligase, is used. When an enzymatic reaction, such as a ligation, is being conducted, it is preferable to provide the elements required for such a reaction in excess, such that the ability to achieve the desired ligation is not limited by the concentration of the elements.

v) PCR Amplification

The use of PCR is well known in the art and is described in U.S. Pat. No. 4,683,202, the contents of which are expressly incorporated herein by reference. The technique is described in several general sources, which provide adequate guidance to one of skill in the art, including Maniatis et al. and "PCR Protocols, A Guide to Methods and Applications" (Innis et al. eds.), Academic Press, San Diego, Calif., 1990. However, other amplification techniques, such as strand displacement amplification (SDA), are known and can be useful in the practice of the subject methods.

C. Synthesis of the Nucleic Acid Component Terminal Sequences

Important elements of the method of the invention are terminal sequences, which are required for the efficient assembly of multiple nucleic acid components. The preferred type of terminal sequence is non-palindromic, even though palindromic terminal sequences or a mixture of palindromic and non-palindromic terminal sequences could be used. That is, the single-stranded overhang is not a product of a restriction enzyme The benefits of using non-palindromic terminal sequences are that there is no possibility of self-ligation and, in general, the terminal sequences may be designed so that only a single pair of terminal. sequences are complementary and will exclusively anneal with each other. The size of the terminal sequences may be varied, but in general, the larger the size of the terminal sequence, the greater the fidelity of annealing specific and complementary terminal sequences within a mixture of numerous other terminal sequences. However, in certain preferred embodiments, the terminal sequences are about 6 to about 20 nucleotides in length, more preferably about 6 to about 15 nucleotides in length, and even more preferably about 6 to about 10 nucleotides in length.

Terminal single-stranded overhang sequences may be provided at either or both of the 5' or 3' ends of the nucleic acid component (e.g., see FIG. 2). Preferably, at least one of the terminal sequences is a non-palindromic overhang. The primary constraint is that a 5' terminal sequence, in general, must anneal with a complementary 5' terminal sequence or an oligonucleotide (or series of oligonucleotides) which provide a complementary 5' terminal sequence. Likewise, a 3' terminal sequence must, in general, anneal with either a complementary 3' terminal sequence or an oligonucleotide (or series of oligonucleotides) which provide a complementary 3' terminal sequence. The use of a bridging oligonucleotide which is complementary to both a 3' overhang on a first nucleic acid component and a 5' vector overhang on a second nucleic acid component is shown in FIG. 2, D. A second strategy for joining two nucleic acid components is by means of a "semi-cruciform" bridging element as shown in FIG. 3. In this embodiment of the joining method, the bridging element is comprised of two separate but partially complementary oligonucleotides which bridge the 5' and 3' overhangs of adjacent nucleic acid components. The semi-cruciform bridged nucleic acid components can then be covalently joined by a ligation step as shown.

Terminal sequences may be synthesized by using a number of different methods including, without limitation, the following:

(1) Adaptors may be ligated to restriction enzyme digested nucleic acid components. These adaptor molecules are composed of synthetic oligonucleotides which are designed to be complementary at one end with a restriction enzyme digested nucleic acid molecule and the other end containing a single stranded terminal sequence, preferably non-palindromic.

(2) Oligonucleotide primers, which contain one or more synthetic uracil residues, may be utilized to PCR-amplify a fragment, followed by uracil DNA glycosylase treatment, resulting in 3' terminal sequences, a method described in U.S. Pat. No. 5,137,814, the contents of which are expressly incorporated herein by reference. "Uracil DNA glycosylase" (UDG), a term of art, refers to an activity which cleaves the glycosidic bond between the base uracil and the sugar deoxyribose, only when the monomeric nucleotide dUTP is incorporated into a DNA molecule, resulting in incorporation of a deoxyuridine moiety (Duncan, B. in *The Enzymes* 14:565 (1981, ed.: Boyer P.). An enzyme possessing this activity does not act upon free dUTP, free deoxyuridine, or RNA (Duncan, supra). The action of UDG results in the production of an "abasic" site. The enzyme does not, however, cleave the phosphodiester backbone of the nucleic acid component. Most preferably, the phosphodiester backbone at an abasic site may be cleaved through the use of an endonuclease specific for such substrates. A preferred enzyme for this purpose is the *E. coli* enzyme, Endonuclease IV. Most preferably, Endonuclease IV is used in conjunction with UDG to remove dU residues from a nucleic acid component.

3) 5' terminal sequences may be generated in PCR products by using PCR oligonucleotide primers containing alkane diol derivatives, a method described in U.S. Pat. No. 5,426,039, the contents of which are expressly incorporated herein by reference. These same type of modified primers may be used when using non-PCR amplification methods, resulting in the same type of unique terminal sequences as defined by these primers.

Figure 4:
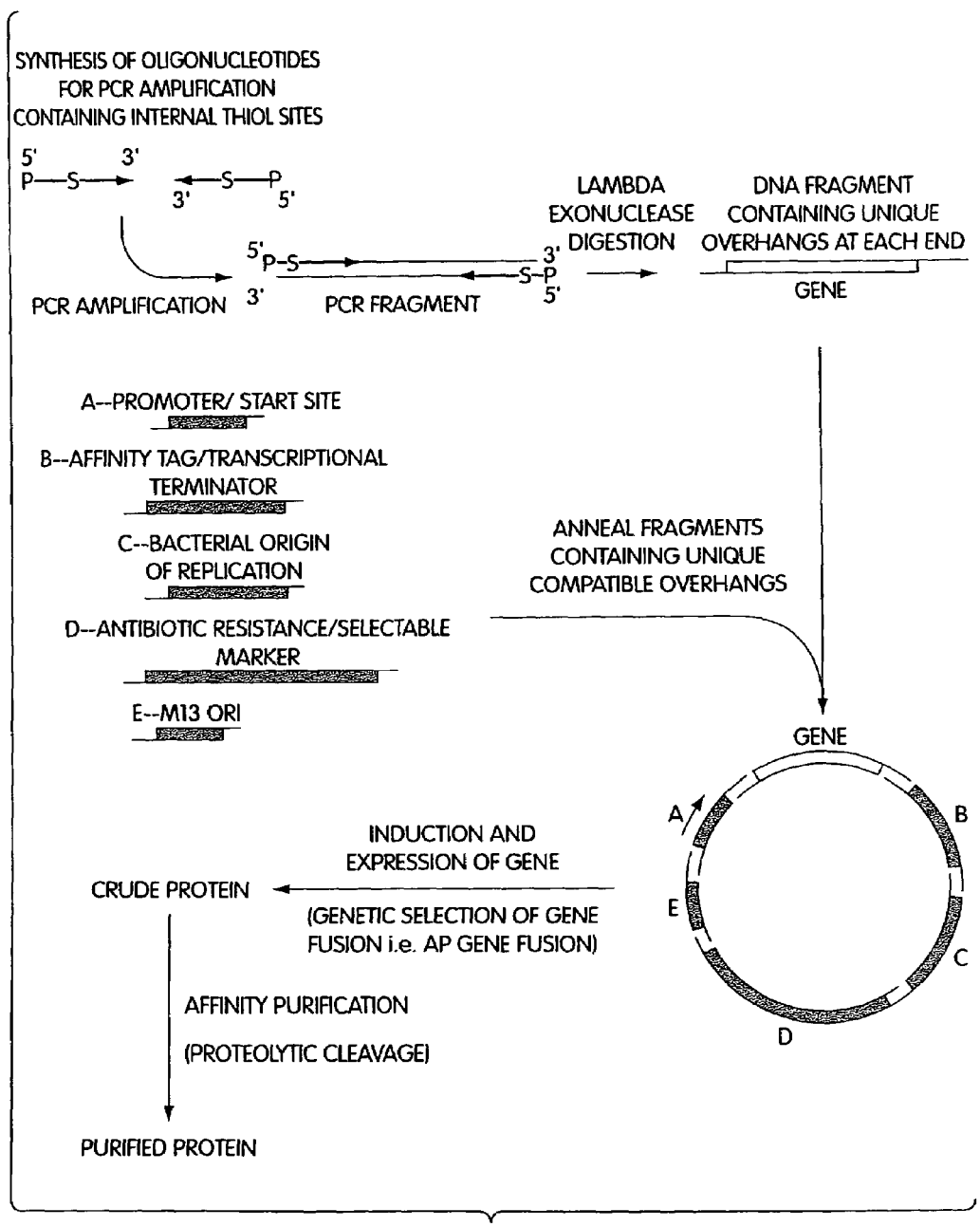
FIG. 4 illustrates a method for introducing unique 3' overhangs at each end of a vector element by a method employing pcr amplification with primers containing a phosphorothioate-nucleotide linkage followed by exonuclease digestion of the amplification product to create unique complementary 3' overhangs in the vector elements to be conjoined.

4) Suitable nucleic acid component 3' terminal sequences may be generated by PCR with phosphorothioate substituted oligonucleotides followed by exonuclease digestion. A particularly preferred method for the synthesis of the nucleic acid terminal sequence component is by a specialized pcr amplification and cloning technique as shown in FIG. 4. The technique produces single-stranded 3' DNA overhangs suitable for joining the nucleic acid components of the present invention. In a preferred embodiment, the 3' overhangs are 12 to 15 nucleotides long. The technique involves incorporating phosphorothioate-nucleotide substituted oligonucleotide primers onto the ends of a target nucleic acid component by means of pcr amplification. The oligonucleotide primers are designed to incorporate the phosphorothioate nucleotide linkage at a specific site within the primers. The substituted linkage is resistant to exonuclease cleavage and so exposure of the nucleic acid component amplification product to an appropriate 5' exonuclease establishes a discrete and stable proximal end to the 3' single stranded overhang on the undigested strand. Suitable exonuclease enzymes include lambda exonuclease, which possesses a 5' to 3' exonuclease activity but no 3' to 5' exonuclease activity. The resulting exonuclease digested phosphorothioate substituted oligonucleotide amplification product will contain unique 3' single-stranded overhangs corresponding in sequence to the complement of the sequence 5' proximal to the phosphorothioate linkage of the primer. Complementary 3' overhangs can be incorporated into a cloning vector which would allow for specific annealing with 3' overhangs of the fragment to be cloned.

In one embodiment of the invention, this 5' phosphorothioate proximal portion of the primer corresponds to a sequence in the target nucleic acid component. In a preferred embodiment, however, this 5' phosphorothioate proximal portion of the primer is uniquely introduced into the pcr product by the amplification process itself. The incorporation of standard restriction endonuclease recognition elements onto the 5' ends of per amplification primers is a well established method of facilitating the cloning of pcr-generated sequences. The standard method involves cleavage of the pcr product with the corresponding restriction endonuclease to create a 5' or 3' overhang. The phosphorothioate-substituted primer/exonuclease digestion method is particularly advantageous over the standard restriction site method in that virtually any sequence (palindromic or nonpalindromic) can be introduced into the 3' overhang. Thus the 3' overhang can be specifically tailored to the application.

Generally, in joining two nucleic acid components in a particular orientation, the pcr primers are designed so that the ends to be joined correspond to complementary 5' regions of the phosphorothioate linkage substituted primers (see FIG. 3). These regions of 5' complementarity are converted into complementary 3' overhangs following pcr amplification and exonuclease treatment as described above. These 3' overhangs can be uniquely adapted so that the various nucleic acid components are joined in only one possible polarized configuration.

The flexibility afforded by this unique manner of introducing 3' overhangs onto any nucleic acid component is particularly suited to the joining of those nucleic acid components which directly affect the expression or form of the insert of interest. This is because expression signal sequences are often affected by the sequences immediately surrounding them. Furthermore, the proteins expressed by nucleic acid components encoding fusion polypeptide domains are often influenced by the polypeptides they are fused to due to the lack of predictability of protein folding and steric relationships between the two joined polypeptides. The immediate invention provides a means of introducing virtually any sequence in these positions and thereby allows the maintenance of optimized function of individualized elements even as they are shuffled in numerous combinations with other elements. This flexibility is particularly suited to the joining of polypeptide-encoding nucleic acid components because the unique 3' overhangs can be uniquely designed to allow for: maintenance of the appropriate reading frame across a polypeptide fusion junction; introduction of small polypeptide-encoding domains, such as the FLAG epitope, between polypeptide-encoding nucleic acid components; and the introduction of particular "floppy" polypeptide-sequences, such as poly-glycine, between polypeptide elements such that the resulting joined polypeptides fold independently and retain independent functions.

In one embodiment, the resulting nucleic acid components containing the terminal sequences, can be isolated by agarose or acrylamide gel electrophoresis followed by elution of the nucleic acid components from the agarose or acrylamide matrix. The two most common ways of elution are either soaking in an appropriate buffer or electroelution, both described in Maniatis et al. Both methods are effective, but soaking is often the method of choice because it is inexpensive, easy and can be accomplished without monitoring. Kits for the purification of nucleic acids from gel matrices may also be used (e.g. "Compass Kit", American Bioanalytical). In another embodiment, the resulting nucleic acid components, containing the terminal sequences, can be purified using reverse phase or anion-exchange HPLC.

D. Covalent Assembly of the Nucleic Acid Components

In the method of the invention, the various nucleic acid components are designed so that each component may contain specific and unique terminal sequences at either end. Each terminal sequence can be designed to anneal and base pair with a unique complementary terminal sequence residing on a separate nucleic acid component A series of specific annealing reactions occur between complementary terminal sequences. This results in the assembly of a larger nucleic acid multicomponent construct having a defined relative order and orientation for all the components.

Figure 2A:
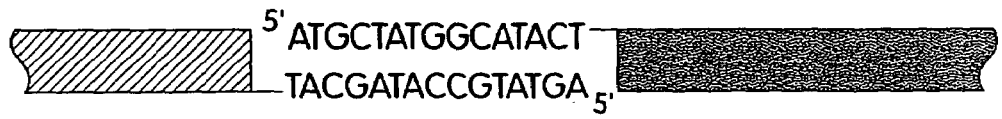
FIG. 2(A) shows annealing of non-palindromic complementary terminal sequences.
Figure 2B:
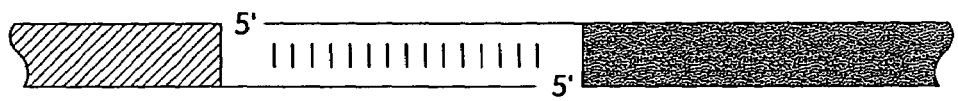
FIG. 2(B) shows annealing of 5' compatible terminal sequences.
Figure 2C:
FIG. 2(C) shows annealing of 3' compatible terminal sequences.
Figure 2D:
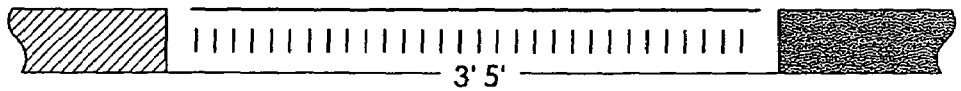
FIG. 2(D) shows linking of non-compatible terminal sequences via an oligonucleotide bridge (thick line)
Figure 2E:
FIG. 2(E) shows linking of non-compatible terminal sequences via an adaptor (thick lines).
Figure 3:
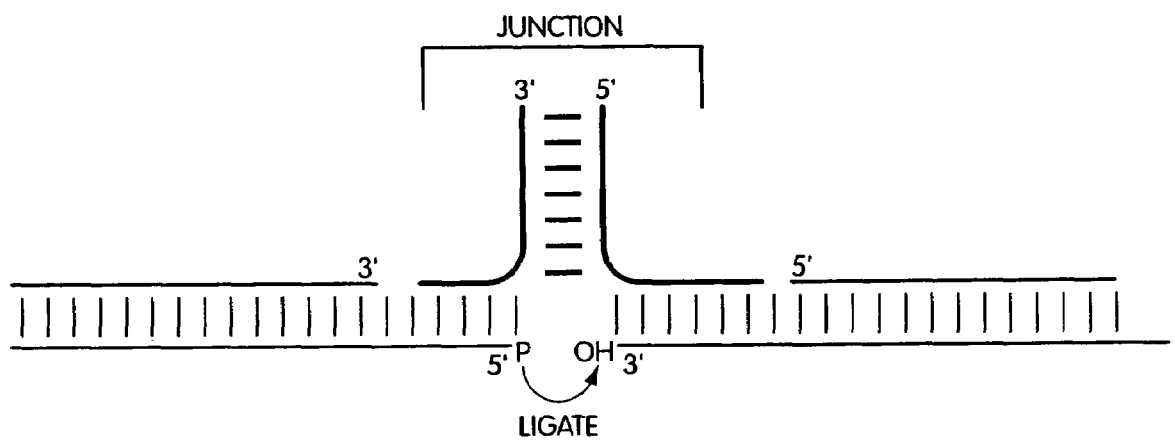
FIG. 3 illustrates a method for linking nucleic acid components via a specific semi-cruciform oligonucleotide bridge (thick line) which itself is composed of two partially complementary oligonucleotides. The two nucleic acid component pieces, one with a 5' overhang and the other with a 3' overhang, are brought together by the semi-cruciform bridge and subsequently covalently joined by a ligation step as shown.

According to the method of the invention, the various nucleic acid components can be linked via, without limitation, the following:

(1) Annealing of 5' complementary terminal sequences in two separate nucleic acid components (FIG. 2B).
(2) Annealing of 3' complementary terminal sequences in two separate nucleic acid components (FIG. 2C).
(3) Annealing of an oligonucleotide bridge with complementary 5' and 3' terminal sequences in two separate nucleic acid components (FIG. 2D).
(4) Annealing of an adaptor molecule with complementary 5' or 3' terminal sequences in two separate nucleic acid components (FIG. 2E).
(5) Annealing of a semi-cruciform bridge comprising two partially complementary oligonucleotides with complementary 5' and 3' terminal sequences in two separate nucleic acid components (FIG. 3).

The fidelity of assembly of the nucleic acid multicomponent construct depends upon a number of factors, including, without limitation, the following: 1) The number of different nucleic acid components, 2) The size of the terminal sequences, 3) The way annealing occurs, 4) The annealing conditions, 5) The nucleotide sequence within the terminal sequences.

In certain embodiments, the generation of multicomponent constructs can be monitored by incorporation of nucleic acid components which include portions of a genetic element(s) which, for its functionality to be apparent, requires the presence of two or more nucleic acid components in the final construct. For example, a marker gene can be split between two nucleic acid components, and is only detected when the gene is recapitulated by successful ligation of the two nucleic acid components.

In a preferred embodiment of the invention, three or more nucleic acid components are used for the production of a nucleic acid construct. Preferably three, four, five, or six nucleic acid components are used and more preferably three to eight nucleic acid components are used. Using the method of the invention, the various nucleic acid components can be incubated either simultaneously or in a step-wise fashion, to form nucleic acid multicomponent constructs which can be either functional as assembled or which can be used as subcomponents for the assembly of functional constructs. Three or more nucleic acid components may be linked to form a nucleic acid multicomponent construct. Functional constructs may be assembled from such nucleic acid multicomponent constructs, with each multicomponent construct essentially performing as a single nucleic acid component in the assembly of a functional construct. Nucleic acid multicomponent constructs would be preferably employed when there are a large number of different nucleic acid components requiring assembly, when there are non-unique terminal sequences within a group of different nucleic acid components, or when the size of the final assembled functional construct is very large. Nucleic acid multicomponent constructs may also be used in repetitive cloning experiments or in the design of assembly reactions which are repetitive or otherwise simplified.

Typically, the nucleic acid components would include an appropriately phosphorylated terminal sequence, suitable for ligation to a separate nucleic acid component. The nucleic acid components are incubated under appropriate conditions that allow for efficient annealing of the complementary terminal sequences. Appropriate annealing conditions are described in Maniatis et al. In a particularly preferred embodiment of the invention, the nucleic acid components are incubated in equimolar concentrations, heated to 65° C., and then cooled down slowly to 25° C. Temperatures ranging from 60 to 75° C. may be used depending on the size of the terminal sequences employed.

In certain embodiments of the invention, the nucleic acid components are treated with a ligase enzyme to ligate the nucleic acid components and produce a nucleic acid construct. Preferably a T4 DNA ligase is used, even though the *E. coli* ligase may also be used for certain applications. In another embodiment of the method of the invention, ligation of the different nucleic acid components may not be necessary prior to transferring the assembled nucleic acid construct into the appropriate biological or experimental system.

In yet another embodiment, the combinatorial method can be carried out in a manner that utilizes flanking intronic sequences to generate a combinatorial library of multicomponent constructs. As illustrated schematically in FIG. 5, the combinatorial event takes place at the DNA level through annealing of complementary sequences within intronic portions of the nucleic acid components. Briefly, double-stranded nucleic acid components are generated which include an "exonic sequence" and flanking intron fragments. That is, intronic sequences flanking the 5' end of an exon module represent a 3' fragment of an intron. As described herein, 5' and 3' non-palindromic overhangs are generated in the nucleic acid components. Annealing of the non-palindromic terminal sequences, therefore, mediates concatenation of the component to one and other through basepairing. In the exemplary illustration of FIG. 5, the exon sequences are flanked by domains IV-VI of an autocatalytic group II intron at one end, and domains I-IV at the other. A library of combinatorial units representative of a number of different exons is generated. Upon annealing of the non-palindromic terminal sequences, the sequences corresponding to domain IV at the 3' end of one unit anneal with the complementary domain IV sequences at the 3' end of another unit, resulting in concatenation of combinatorial units (see FIG. 5).

The resulting combinatorial genes can be subsequently cloned into an expression vector. In one instance, 5' terminal and 3' terminal combinatorial units can be used and the double-stranded genes can be amplified using PCR anchors which correspond to sequences in each of the two terminal units. The PCR primers can further be used to add restriction endonuclease cleavage sites which allow the amplified products to be conveniently ligated into the backbone of an expression vector. Upon transcription of the combinatorial gene, the intronic RNA sequences will drive ligation of the exonic sequences to produce an intron-less transcript. In this manner, the subject GEOS method can be used to introduce non-palindromic overhangs in the nucleic acid components without altering the coding sequence.

Figure 5:
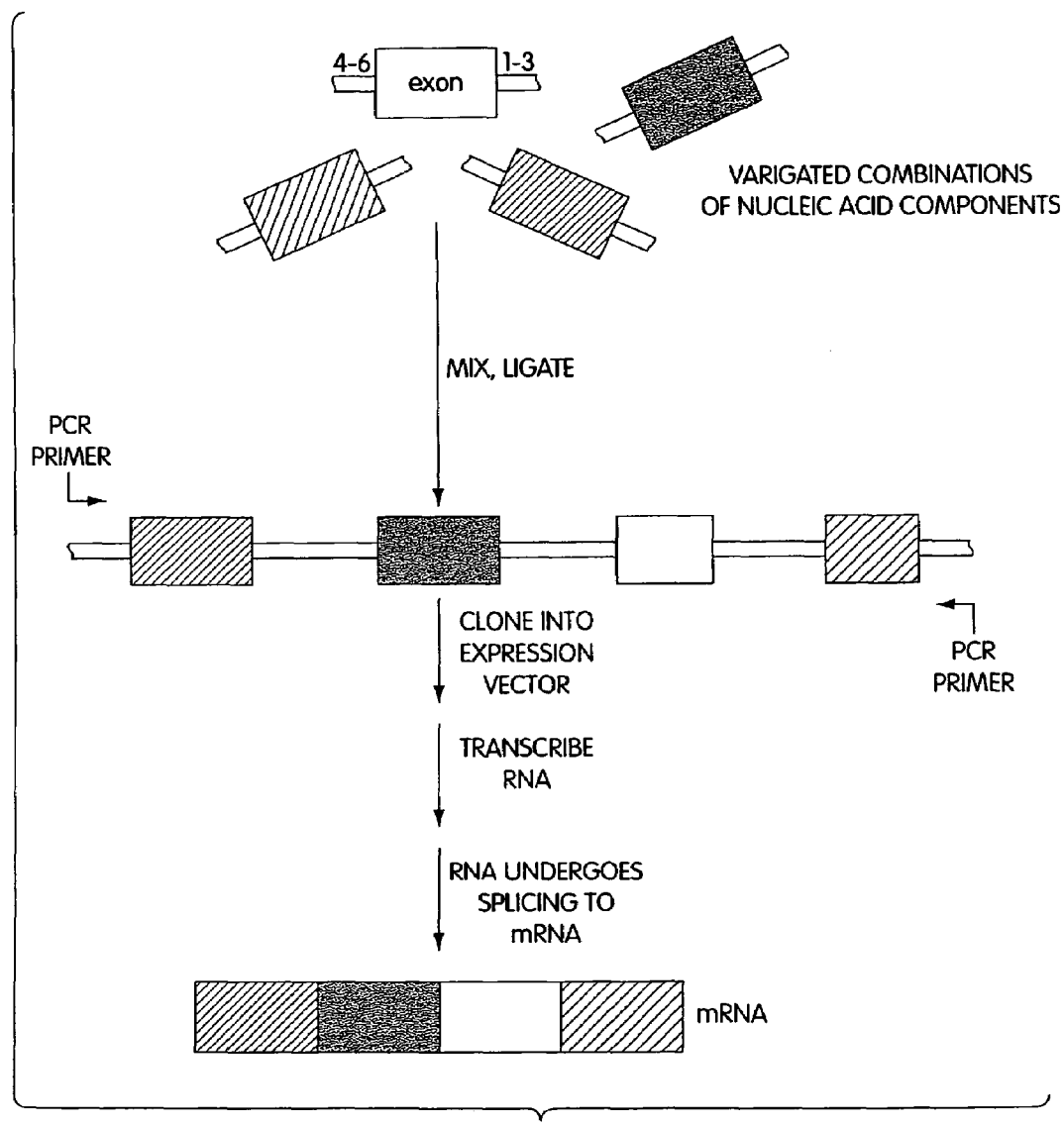
FIG. 5 is a schematic representation of a illustrative method for carrying out the subject GEOS combinatorial method in a manner that utilizes flanking intronic sequences to generate a combinatorial gene library.

While FIG. 5 demonstrates one embodiment which utilizes group II introns, the combinatorial process can be carried out in similar fashion using either group I intron sequences or nuclear pre-mRNA intron sequences.

As used herein, the terms "exon" and "exonic sequence" denotes nucleic acid sequences, or exon "modules", that can, for instance, encode portions of proteins or polypeptide chains, such as corresponding to naturally occurring exon sequences or naturally occurring exon sequences which have been mutated (e.g. point mutations, truncations, fusions), as well as nucleic acid sequences from "synthetic exons" including sequences of purely random construction. However, the term "exon", as used in the present invention, is not limited to protein-encoding sequences, and may comprises nucleic acid sequences of other function, including nucleic acids of "intronic origin" which give rise to, for example, ribozymes or other nucleic acid structure having some defined chemical function.

E. Preparation of Synthetically or Covalently Modified Nucleic Acid Components

A unique feature of the method of the invention is that, since nucleic acid components may be made synthetically, any nucleic acid component may be altered or modified to contain one or more modifications (i.e., handles). Handles may act as sites of attachment for small biological molecules or macromolecular biological molecules, including proteins or carbohydrates. They may also serve as sites of attachment for chemically synthesized, non-biological molecules. The method of the invention, therefore, enables users to synthesize constructs having altered biological properties.

Modifications which could be performed on nucleic acid components include, without limitation, the following: Modification of nucleic acid residues, biotinylation, fluorescent tagging, incorporation of polypeptide nucleic acids (PNA), covalent or non-covalent conjugation of proteins involved in nucleic acid modification (e.g. through the use of activated boronic acid moieties), including enzymes, covalent or non-covalent conjugation of proteins or other components or ions which enable the recognition and binding of specific molecular targets, including haptens.

Modification of nucleic acid residues can be performed by a variety of art known techniques. The simplest method for performing oligonucleotide directed mutagenesis is by enzymatic primer extension (PCR). In this method, an oligonucleotide primer is designed that carries the mutation of interest flanked by 10 to 15 nucleotides of wild-type sequence. This "mutagenic" oligonucleotide can then be used in a PCR reaction along with an oligonucleotide primer containing one or more synthetic uracil residues or alkane diol derivatives to create the nucleic component of interest. The types of mutations that can be made by this approach range from single nucleotide substitutions to deletions or insertions, limited only by the size of the oligonucleotide primer needed.

The synthesis of biotinylated nucleotides is well known in the art and was first described by Langer et al. (PNAS 78:6633-37, 1981). Biotin, a water soluble vitamin, is covalently attached to the C5 position of the pyrimidine ring via an allylamine linker arm. Biotinylation of DNA can be achieved by either nick translation, adapted successfully to incorporate biotinylated nucleotides (biotin-11 and biotin-16-dUTP, biotin-14-dATP), or random-priming using biotinylated octamers. Biotinylated nucleic acid molecules can be prepared from biotin-NHS (N-hydroxy-succinimide) using techniques well known in the art (e.g., biotinylation kit, Pierce Chemicals, Rockford, Ill.).

Fluorescent tagging of nucleic acid molecules can be performed using techniques well known in the art (e.g. using the Fluore-dUTP Labelling Mix by Pharmacia) Examples of suitable fluorescent materials include umbelliferone, fluorescein, fluorescein isothiocyanate, rhodamine, dichlorotriazinylamine fluorescein, dansyl chloride or phycoerythrin.

In an embodiment of the invention, synthetic oligonucleotides are used that contain polypeptide nucleic acids or functional groups like primary amines, sulfhydryls, disulfides, and any other group typically used for conjugation of haptens, proteins, enzymes or antibodies.

F. GEOS Nucleic Acid Components

Another aspect of the invention pertains to the assembly of vectors, preferably expression vectors, using a series of interchangeable nucleic acid components or "vector elements". As used herein, the term "vector" refers to a nucleic acid molecule capable of transporting another nucleic acid to which it has been linked. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

The invention provides methods for the rapid assembly of multi-element vector systems in which one or more of the various elements of the expression system can be varied so as to create a collection of candidate expression clones from which optimization of expression can be achieved by appropriate screening or selection techniques. Those elements to be included in any vector system will depend upon the system's intended use. Furthermore those elements of the multi-element system to be systematically varied will further depend upon both its intended use as well as the nature of difficulties anticipated in achieving suitable expression in a given context. The method is particularly suited to the production of complex pools of expression vectors in which one or more nucleic acid components are varied. Such pools may serve as "libraries" of candidate expression vectors from which particular species may be selected on the basis of preferred properties. Alternatively, the heterogeneous pools may be directly useful in applications for which expression of heterogeneous populations of related species may be desirable (e.g. DNA vaccines).

The vector elements can be roughly divided into two categories: those which directly affect the expression or form of the insert of interest and those which do not (i.e. vector "backbone" elements). Examples of the former include: promoter elements, enhancer elements, transcription initiation elements, transcription termination elements, polyadenylation signal elements, intronic elements, translation initiation elements, epitope tag elements, and various polypeptide fusion elements. Examples of the latter typically include: selectable marker elements, origin of replication elements, integration elements, integration-promoting factor elements, and chromosomal structural elements such as centromeric attachment elements and telomeric elements.

Preferred promoter vector elements of the present invention include both eukaryotic and prokaryotic promoter elements. Preferred prokaryotic promoter elements of the invention include those which carry optimal −35 and −10 (Pribnow box) sequences for transcription by RNA polymerase in *Escherichia coli*. Some prokaryotic promoter elements will contain overlapping binding sites for regulatory repressors (e.g. the Lac, and TAC promoters, which contain overlapping binding sites for lac repressor thereby conferring inducibility by the substrate homolog IPTG). Examples of prokaryotic genes from which suitable promoter sequences may be obtained include *E. coli* lac, ara, and trp. Prokaryotic viral promoter elements of the present invention include lambda phage promoters (e.g. $P_{RM}$ and $P_R$), T7 phage promoter elements, and SP6 promoter elements. Eukaryotic promoter vector elements of the invention include both yeast (e.g. GAL1, GAL10, CYC1) and mammalian (e.g. promoters of globin genes and interferon genes). Preferred eukaryotic promoter vector elements include viral gene promoters such as those of the SV40 promoter, the CMV promoter, herpes simplex thymidine kinase promoter, as well as any of various retroviral LTR promoter elements (e.g. the MMTV LTR). Still more preferred eukaryotic promoter vector elements contain both a control region in addition to a promoter so that the resulting construct can be derepressed by a suitable inducing agent. Examples of such control regions include those which bind the tetracycline resistance repressor, specific forms of which can cause regulated activation or repression of a linked promoter in response to tetracycline.

Promoter vector elements of the invention include both inducible and repressible promoters. The inducible promoters of the present invention include those which are capable of functioning in a eukaryotic host organism. Preferred embodiments include naturally occurring yeast and mammalian inducible promoters as well as synthetic promoters designed to function in a eukaryotic host as described below. The important functional characteristic of the inducible promoters of the present invention is their ultimate inducibility by exposure to an environmental inducing agent. Appropriate environmental inducing agents include exposure to heat, various steroidal compounds, divalent cations (including $Cu^{+2}$ and $Zn^{+2}$), galactose, tetracycline, IPTG (isopropyl b-D thiogalactoside), as well as other naturally occurring and synthetic inducing agents and gratuitous inducers. In certain modes of the invention, the environmental inducing signal can correspond to the removal of any of the above listed agents which are otherwise continuously supplied in the uninduced state (see the tTA based system described below for example). The inducibility of a eukaryotic promoter can be achieved by either of two mechanisms included in the method of the present invention. Suitable inducible promoters can be dependent upon transcriptional activators which, in turn, are reliant upon an environmental inducing agent. Alternatively the inducible promoters can be repressed by a transcriptional repressor which itself is rendered inactive by an environmental inducing agent. Thus the inducible promoter can be either one which is induced by an environmental agent which positively activates a transcriptional activator, or one which is derepressed by an environmental agent which negatively regulates a transcriptional repressor. We note here that the latter class of inducible promoter systems defines transcriptional repressors and corresponding negative cis regulatory elements which can also fund use as the repressors and corresponding repressible promoters of the present invention as described in section 4.3.2.

The inducible promoters of the present invention include those controlled by the action of latent transcriptional activators which are subject to induction by the action of environmental inducing agents. Preferred examples include the copper inducible promoters of the yeast genes CUP1, CRS5, and SOD1 which are subject to copper-dependent activation by the yeast ACE1 transcriptional activator (see e.g. Strain and Culotta (1996) Mol Gen Genet 251: 139-45; Hottiger et al. (1994) Yeast 10: 283-96; Lapinskas et al. (1993) Curr Genet 24: 388-93; and Gralla et al. (1991) Proc. Natl. Acad. Sci. USA 88: 8558-62). Alternatively, the copper inducible promoter of the yeast gene CTT1 (encoding cytosolic catalase T), which operates independently of the ACE1 transcriptional activator (Lapinskas et al. (1993) Curr Genet 24: 388-93), can be utilized. The copper concentrations required for effective induction of these genes are suitably low so as to be tolerated by most cell systems, including yeast and $Drosophila$ cells. Alternatively, other naturally occurring inducible promoters can be used in the present invention including: steroid inducible gene promoters (see e.g. Oligino et al. (1998) Gene Ther. 5: 491-6); galactose inducible promoters from yeast (see e.g. Johnston (1987) Microbiol Rev 51: 458-76; Ruzzi et al. (1987) Mol Cell Biol 7: 991-7); and various heat shock gene promoters. Many eukaryotic transcriptional activators have been shown to function in a broad range of eukaryotic host cells, and so, for example, many of the inducible promoters identified in yeast can be adapted for use in a mammalian host cell as well. For example, a unique synthetic transcriptional induction system for mammalian cells has been developed based upon a GAL4-estrogen receptor fusion protein which induces mammalian promoters containing GAL4 binding sites (Braselmann et al. (1993) Proc Natl Acad Sci USA 90: 1657-61). These and other inducible promoters responsive to transcriptional activators which are dependent upon specific inducing agents are suitable for use with the present invention.

The inducible promoters of the present invention also include those which are repressed by repressors which are subject to inactivation by the action of environmental inducing agents. Examples include prokaryotic repressors which can transcriptionally repress eukaryotic promoters which have been engineered to incorporate appropriate repressor-binding operator sequences. Preferred repressors for use in the present invention are sensitive to inactivation by physiologically benign inducing agent. Thus, where the lac repressor protein is used to control the expression of a eukaryotic promoter which has been engineered to contain a lacO operator sequence, treatment of the host cell with IPTG will cause the dissociation of the lac repressor from the engineered promoter and allow transcription to occur. Similarly, where the tet repressor is used to control the expression of a eukaryotic promoter which has been engineered to contain a tetO operator sequence, treatment of the host cell with IPTG will cause the dissociation of the tet repressor from the engineered promoter and allow transcription to occur.

In a preferred embodiment of the invention, the repressor of the inducible promoter is synthesized as a ubiquitin fusion protein conforming to the formula ubiquitin-X-repressor. This can be achieved using the ubiquitin fusion vector systems designed to confer inducible proteolytic sensitivity to the target gene polypeptide as described below. Thus it will be appreciated by the skilled artisan that a rapid induction of a repressible promoter can be achieved by simultaneously delivering an environmental inducing agent which causes dissociation of the repressor from the repressed inducible promoter, and simultaneously promoting the destruction of that repressor by N-end rule directed proteolysis. Degradation of the repressor prevents rebinding to the operator which can result in decreased inducibility of the repressible promoter—a problem which has been recognized in the art (see Gossen et al. (1993) TIBS 18: 471-5). Furthermore, this aspect of the invention can be utilized independently of the targeted shut-off of a gene, to generally increase the inducibility of a eukaryotic expression system which is subject to repression by a repressor. Thus the present invention further provides improved methods for inducible expression of endogenous or heterologous genes in a eukaryotic cell.

As suggested above, the inducible promoters of the present invention include those which are not naturally occurring promoters but rather synthetically derived inducible promoter systems which may make use of prokaryotic transcriptional repressor proteins. The advantage of using prokaryotic repressor proteins in the invention is their specificity to a corresponding bacterial operator binding site, which can be incorporated into the synthetic inducible promoter system. These prokaryotic repressor proteins have no natural eukaryotic gene targets and affect only the effector of suppression gene which is put under the transcriptional control of the inducible synthetic promoter. This system thereby avoids undesirable side-effects resulting from unintentional alteration of the expression of nontargeted eucaryotic genes when the inducible promoter is induced. A preferred example of this type of inducible promoter system is the tetracycline-regulated inducible promoter system. Various useful versions of this promoter system have been described (see Shockett and Schatz (1996) Proc. Natl. Acad. Sci. USA 93: 5173-76 for review). As suggested above, these tetracycline-regulated systems generally make use of a strong eucaryotic promoter, such as human cytomegalovirus (CMV) immediate early (IE) promoter/enhancer and a tet resistance operator (tetO) which is bound by the tet repressor protein. In a preferred embodiment, the system involves a modified version of the tet repressor protein called a reverse transactivator (rtTA, or rtTA-nls, which contains a nuclear localization signal) which binds tetO sequences only in the presence of the tet derivatives doxycycline or anhydrotetracycline. Using this system, a synthetic human CMV/IE-tetO-promoter driven construct could be induced by 3 orders of magnitude in 20 hrs by the addition of the tet derivatives (see Gossen et al. (1995) Science 268: 1766-9). Thus this system can be used to make the effector of suppression genes of the present invention inducible in response to the delivery of tetracycline derivatives to the targeted eucaryotic cell. Alternatively, a tet repressor fused to a transcriptional activation domain of VP16 (tTA) can be used to drive expression of the inducible promoter of the present invention. In this instance, transcriptional activation of a synthetic human CMV/IE-tetO-promoter driven construct is achieved by the removal of tetracycline since the tTA activator only binds to the tetO in the absence of tet (see Gossen and Bujard (1992) Proc. Natl. Acad. Sci. USA 89: 5547-51). Other synthetic inducible promoter systems are also available for use in the present invention. For example, a lac repressor- VP16 fusion which exhibits a "reverse" DNA binding phenotype (i.e., analogous to rtTA described above, it only binds the lacO operator sequence in the presence of the inducer IPTG) (see Lambowitz and Belfort (1993) Annu Rev Biochem 62: 587-622). This particular synthetic inducible promoter is approximately 1000-fold inducible in the presence of IPTG. Since neither the tet repressor gene nor the lac repressor gene occurs naturally in a eukaryotic cell, systems involving synthetic inducible promoter constructs such as these rely on the further delivery of an expressible copy of the appropriate prokaryotic repressor gene. Suitable expression cassettes for this purpose are readily available for heterologous expression in many different eukaryotic cells including various yeast species and mammalian cells.

Another vector element category for use in the present invention is a eukaryotic enhancer element. Preferred eukaryotic enhancer elements include those which are tissue and/or developmentally specific. Incorporation of such tissue-specific vector elements by GEOS methodology can be particularly useful in gene therapy applications in which only a specific human tissue is targeted for expression. Other enhancers elements for use in the present invention include viral transcriptional enhancers such as the SV40 enhancer, the polyoma virus enhancer, and retroviral LTR enhancers. Preferred viral enhancer elements exhibit strong cell-type preference in transcriptional activity. Examples include enhancer elements within the Moloney MuSV, which are regulated by the glucocorticoid dexamethasone and a hepatitis B enhancer associated with a hepatitis surface antigen coding sequence which is specifically active in human liver cells.

Yet another vector element of the present invention is fusion polypeptide-encoding element which can be fused to the coding region of any insert gene of interest. For example, in certain applications it is useful to be able to mark a particular gene product with a tag so that the localization and function of the gene product can be easily monitored. A particularly preferred version of a molecular tag fusion polypeptide element is the green fluorescent protein or GFP (see e.g. Misteli and Spector (1997) Nature Biotechnology 15: 961-4; and Gerdes and Kaether (1996) FEBS Lett 389: 44-7 for review). This fusion tag polypeptide emits green (approximately 510 nm wavelength) light upon excitation by a particular wavelength of incident light (approximately 400 to 480 nm, depending upon the form of GFP). Various versions of GFP coding sequences, including those whose codon usage has been humanized and those whose emission spectra have been "red-shifted," are commercially available and can be readily adapted to GEOS methodology. Applications of GFP include in situ localization of a linked gene of interest, as well as facile monitoring of expression and tropism in various cell mediated expression studies.

Still other vector element fusion polypeptides include beta-galactosidase and thioredoxin, as well as various affinity tags (e.g. polyHIS, which binds with high affinity to a columns to which $Ni^{+2}$ is immobilized) and epitope tags, which are particularly suited to subsequent detection with corresponding antibodies (e.g. myc, FLAG, enterokinase, or hemagluttinin tags). Various epitope tag encoding sequences are available and can be readily adapted to GEOS methodology.

Yet another class of vector elements for use in the invention are transcriptional terminator elements which promote the formation of 3' ends in a mature RNA transcript. Such elements include prokaryotic terminator elements as well as eukaryotic terminator elements which function primarily as polyadenylation signals. Examples of the latter included various viral terminator elements such as the SV40 polyadenylation signal element and the beta-globin polyadenylation signal element.

In a particularly preferred embodiment of the invention, the vector elements comprise exonic and intronic units which can used to facilitate rearrangement of discrete polypeptide-encoding exon units. The GEOS methodology thereby facilitates the formation of peptide domain "shuffled" libraries encoded by exonic units which are linked by intronic units. Thus GEOS can be readily applied to the creation of unique proteins peptide domain shuffling and in vitro selection techniques. In one particular embodiment of the peptide domain shuffling application a pool of diverse peptide domain-encoding nucleic acid components is added to a GEOS vector assemblage. A compatible intronic unit is then added prior to the addition of another pool of diverse peptide domain-encoding exonic nucleic acid components. The resulting GEOS assembly increases in heterogeneity with successive addition of peptide domain-encoding components and provides a convenient source of diversity for subsequent screening or selection processes. GEOS methodology thereby enables the user to create synthetically "evolved" proteins comprised of discrete polypeptide domains which have been randomized and infinitely "shuffled."

A discussion of general considerations to be made in designing suitable vector systems is provided below.

One type of vector produced by the method of the invention is a minimal vector (referred to usually as a plasmid vector), which is basically a circular double stranded DNA loop into which additional DNA segments can be ligated. Another type of vector, produced by the method of the invention, is a vector capable of directing the expression of genes to which it is operatively linked. Such a vector is referred to herein as an "expression vector". The invention is intended to include the production of various forms of expression vectors, such as vectors derived from bacteriophage, including all DNA and RNA phage (e.g. cosmids), or viral vectors derived from: (a) all eukaryotic viruses, such as baculoviruses and retroviruses, (b) adenoviruses and adeno-associated viruses, Herpes viruses, Vaccinia viruses and all single-stranded, double stranded and partially double stranded DNA viruses, (c) all positive and negative stranded RNA viruses, and (d) replication defective retroviruses.

Another type of vector produced by the method of the invention is a yeast artificial chromosome (YAC), which contains both a centromere and two telomeres, allowing YACs to replicate as small linear chromosomes. YACs can carry several hundred thousand base pairs of DNA, making them appropriate for genome mapping procedures. Other artificial chromosomes include the PAC (P1 artificial chromosomes), BAC (bacterial artificial chromosomes) and MAC (mammalian artificial chromosomes), or exogenous extra-chromosomal components, e.g., derived from viruses and other cellular parasites.

Each nucleic acid component involved in the assembly of a vector construct is intended to encode a specific biological functionality or multiple functionalities. For example, plasmid vectors generally contain several genetic elements such as the following: (a) an origin of replication, (b) a selectable marker element, (c) an insert of interest, for the insertion of genetic elements, such as a specific gene coding for a protein of interest.

The method of the present invention enables nucleic acid components to be synthesized to contain specific and unique terminal sequences such that annealing of complementary terminal sequences between different components will result in the generation of definable and specifically oriented constructs. A vector may be constructed by combining a set of nucleic acid components which provide all the necessary genetic elements required to generate a functional vector, while the unique terminal sequences on each component will determine the order in which all of the nucleic acid components are assembled relative to each other.

According to the method of the invention, individual nucleic acid components may be substituted with other components containing the same unique terminal sequences (see FIG. 1). For example, the plasmid origin of replication (ori) is a genetic element of a particular category, whose function is to initiate and regulate plasmid replication in bacteria, provide host range specificity, and regulate plasmid copy number and plasmid compatibility. This general functionality may be provided by a variety of different nucleic acid components within the ori category, including ori segments, ori genes or ori genetic elements. This invention allows for the synthesis and utilization of a series of different ori nucleic acid components, each having the same unique terminal sequences, which would enable users to rapidly and easily choose from a catalog of interchangeable ori nucleic acid components when designing and specifying a plasmid construct. Examples of origins of replication include the pMB1, p15A, 2µ, ColE1, psc101, F, R6K, R1, RK2, and λdv origins of replication.

"Selectable marker" as used herein, refers to the marker and to the nucleic acid encoding said marker. Selectable markers contemplated by the present invention include resistance to antibiotics such as ampicillin, tetracycline, chloramphenicol, kanamycin, neomycin, rifampicin, carnebicillin, streptomycin, and the like. The selectable markers also encompass resistance to drugs such as hygromycin and methotrexate, heavy metals such as cadmium, phage infection, and sensitivity to enzymes which affect calorimetric changes such as β-galactosidase.

A vector may be assembled from multiple individual nucleic acid components, including, without limitation, nucleic acid components which incorporate one or more of the following: (a) origin of replication (bacterial, viral, phage, yeast, mammalian, eukaryotic), (b) selectable markers (antibiotic resistance, drug resistance, mutagenic resistance), (c) promoters (phage, bacterial, yeast, eukaryotic, mammalian), (d) regulatory elements or genes (repressors, enhances), (e) structural genes, (f) fragments of structural genes, (g) translational elements (Shine-Delgarno element, Kozak sequence), (h) terminators of transcription, (i) regulators of mRNA stability (degradation signals, translational regulators), (j) protein encoded elements specifying cellular location (leader sequence, KDEL, CAAX box, nuclear targeting elements), (k) recombination elements (Lox-CRE, M13 ori), (l) mutagenized genes, (m) protein domain encoded regions, (n) synthetic multiple cloning sites, (o) unique restriction enzyme or DNA cleavage sites, (p) site for covalent or non covalent attachment of a biological or chemical molecule (see "Handle").

In a preferred embodiment of the invention, an expression vector is produced. The expression vector produced by the method of the invention comprises nucleic acid components encoding one or more regulatory sequences, selected on the basis of the host cells to be used for expression, as well as the nucleic acid sequence to be expressed. The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors produced by the method of the invention can be introduced into host cells to thereby produce proteins or peptides, including fusion proteins or peptides.

The expression vectors produced by the method of the invention can be, for example, designed for expression of a gene of interest in prokaryotic or eukaryotic cells. For example, the expression vectors can be used for expression in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the expression vectors produced by the method of the invention can be transcribed and translated in vitro, for example using the T7 promoter regulatory sequences and the T7 polymerase. The expression vectors produced by the method of the invention can also be used to produce nonhuman transgenic animals. Furthermore, the nucleic acid vectors produced by the method of the invention can be used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054-3057). Vector constructs assembled using the method of the invention may also be used as templates to synthesize RNA using standard methods. Examples of RNA molecules which could be made, would include, without limitation, the following: mRNA, tRNA, rRNA, snRNA, hnRNA, viral or phage RNA, or modified RNA genes or genetic elements.

G. Assembly of Genomic and cDNA Libraries i) Genomic Libraries

One aspect of the present invention pertains to the assembly of genomic libraries from individual nucleic acid components. Using the method of the invention, eukaryotic organism (e.g. viral) or prokaryotic organism (e.g. phage) genomes may be assembled in unique ways. The genome of an organism may be endonucleolytically or exonucleolytically cleaved using suitable restriction enzymes, followed by ligation of specific adaptor molecules, as described above.

For example, in one embodiment, the Lambda phage genome which is an approximately 50 kb double stranded DNA molecule encoding multiple genetic regulatory elements as well as approximately 30-40 structural genes, can be provided in the form of nucleic acid components. Toward this end, each of the Lambda phage genes, or groups of genes can be synthesized to contain unique terminal sequences so that these genes, or groups of genes may be rapidly and efficiently assembled in a specific order and orientation relative to each other.

In still another embodiment of the method of the invention, partial or complete eukaryotic or prokaryotic genomes may be both assembled and modified simultaneously. The method of the invention enables users to alter or mutagenize one or more of the genes or gene fragments, resulting in the creation of genetic alterations such as a mutated gene, a gene deletion, an enhanced gene function, a fusion gene, an altered regulation of the gene functionality, an addition or deletion of restriction enzyme sites or an addition of a site for covalent or non-covalent attachment of a biological or chemical molecule ("handle").

Viral genomic libraries can be created, for example, for the following viruses: (a) all bacteriophage, including all DNA and RNA phage, (b) all eukaryotic viruses, such as baculoviruses and retroviruses, (c) adenoviruses and adeno-associated viruses, Herpes viruses, Vaccinia viruses and all single-stranded, double stranded and partially double stranded DNA viruses, (c) all positive and negative stranded RNA viruses, and (d) replication defective retroviruses.

ii) Assembly of cDNA Libraries

Another aspect of the present invention pertains to the assembly of cDNA libraries from individual nucleic acid components. Genes or gene fragments derived from mRNA may be assembled in a manner similar to the above, by synthesizing the resulting cDNA molecules so that they contain unique, and in general, non-palindromic terminal sequences. Such cDNA molecules may then be assembled into eukaryotic or prokaryotic expression vectors. This would allow users to choose from a variety of nucleic acid components derived from cDNA and rapidly and flexibly assemble cDNA libraries. Conventional molecular methods could then be used to select or screen these libraries for the clone or clones of interest.

In the method of the invention, cDNA would be made from mRNA according to art known techniques, described in Maniatis et al., using slight modifications. The method of the present invention uses modified oligonucleotide primers, containing uracil or alkane diol derivatives as described above, to synthesize a first strand of cDNA resulting in the formation of a unique terminal sequence at the 3' end of the gene. An engineered adaptor, as described above, may be then ligated to the 5' end of a double stranded cDNA molecule, resulting in a unique terminal sequence at the other end of the molecule. The resulting nucleic acid components, encoding the various cDNA molecules, would then be used along with other nucleic acid components encoding appropriate genetic elements, to assemble cDNA library expression vectors.

H. Solid Phase Synthesis

In one embodiment of the method, the nucleic acid components can be linked sequentially to form the nucleic acid construct. This unique attribute lends itself to the automation of construct assembly. The method of the invention uses, preferably, attachment to a solid support as a starting point in the assembly of a series of nucleic acid components, in a defined order, to form a multicomponent nucleic acid construct.

For example, the initial nucleic acid component is attached to a solid support by methods known in the art. Additional nucleic acid components, designed to contain unique terminal sequences at either end, are added in a step-wise fashion, as single components or non-functional multicomponent constructs, and the assembly of components is based on the specific annealing of complementary terminal sequence pairs as previously described. Nucleic acid components may be ligated together, using a ligase enzyme, after each nucleic acid component addition step in the assembly of the larger construct. Unligated DNA fragments may be removed by washing the solid support. Following synthesis, the assembled multicomponent construct or functional construct may be subsequently cleaved from the solid support.

Examples of solid supports that can be used, for the attachment of the initial nucleic acid component, include cellulose, synthetic polymeric material such as modified polystyrenes or polydimethyl acrylamides, and controlled-pore glass. The assembled nucleic acid construct may be cleaved from the solid support by, for example, ammonium hydroxide treatment. Alternatively, the initial nucleic acid component attached to the solid support could be designed to contain a unique restriction site that would be cleaved upon treatment with the appropriate enzyme to release the assembled to nucleic acid construct in solution.

I. Kits

The reagents required to practice the method of the invention may be provided in the form of a kit. A kit would comprise, in separate containers, the nucleic acid components to be assembled into a construct, and optionally linking nucleic acid molecules as well as buffers, enzymes (e.g., ligase, Klenow, etc)) and an instructional brochure explaining how to use the kit. In a preferred embodiment the kit would provide the nucleic acid components in an appropriately phosphorylated form for ligation.

The invention further provides a kit for the production of vectors. In one embodiments, the kit for the production of vectors would minimally comprise nucleic acid components encoding origins of replication and selectable markers and optionally, transcriptional regulatory sequence(s). The kit could also include nucleic acid components encoding other vector functions (e.g. a promoter, a transcription or translation regulatory element, etc.).

J. Illustrative Applications Employing the Constructs of the Invention

The nucleic acid constructs produced by the method of the invention, can be employed in an application selected from the group consisting of prokaryotic, eukaryotic (mammalian or non-mammalian) expression. For example, the expression vectors can be used for expression in bacterial cells such as *E. coli*, insect cells (using baculovirus expression vectors) yeast cells or mammalian cells or they can be transcribed and translated in vitro, for example using the T7 promoter regulatory sequences and the T7 polymerase. Alternatively, the nucleic acid constructs can be employed in the construction of unique cDNA libraries, protein, antibody and peptide phage display libraries. Kits for screening phage display libraries are commercially available (e.g., the Stratagene *SurfZAP*™ *Phage Display Kit*, Catalog No. 240612). The constructs can further be employed in gene transfer, gene therapy, and the creation of transgenic organisms, as described above. Finally, vector constructs assembled using the method of the invention may also be used as templates to synthesize RNA using standard methods. Examples of RNA molecules which could be made, would include, without limitation, the following: mRNA, tRNA, rRNA, snRNA, hnRNA, viral or phage RNA, or modified RNA genes or genetic elements.

i) GEOS Optimization of Gene Therapy Vectors

DNA-based gene therapy techniques require efficient import of the therapeutic DNA construct into the target cell nucleus where expression occurs. In one aspect, the subject method can be utilized for optimization of a gene therapy vector, e.g., in order to optimize such features as selectivity (tropism), control of gene expression, immunogenicity, and the like, as well as for optimization of a therapeutic protein or nucleic acid expressed by such gene therapy constructs. In this manner, the GEOS method can also be used for the development of safe viral vectors, e.g., is to prevent the generation of replication-competent virus during vector production in a packaging cell line or during gene therapy treatment of an individual.

In one embodiment, the subject GEOS method is applied to the optimization of a gene therapy vector based on a retrovirus, an adenovirus, an adeno-associated virus, a Herpes virus, an HIV virus or other lentivirus, and the like.

In an illustrative embodiment, the subject method is used to optimize the specifity (e.g., infectivity and/or gene expression) of an adenoviral vector for a particular tissue type, such as smooth muscle cells. Adenovirus is a nuclear DNA virus with a genome of about 36 kb, which has been well-characterized through studies in classical genetics and molecular biology (Horwitz, M. S., "Adenoviridae and Their Replication," in Virology, 2nd edition, Fields, B. N., et al., eds., Raven Press, New York, 1990). The genome is classified into early (known as E1-E4) and late (known as L1-L5) transcriptional units, referring to the generation of two temporal classes of viral proteins. The demarcation between these events is viral DNA replication.

Adenovirus-based vectors offer several unique advantages, including tropism for both dividing and non-dividing cells, minimal pathogenic potential, ability to replicate to high titer for preparation of vector stocks, and the potential to carry large inserts (Berkner, K. L., Curr. Top. Micro. Immunol. 158:39-66, 1992; Jolly, D., Cancer Gene Therapy 1:51-64, 1994). The cloning capacity of an adenovirus vector is about 8 kb, resulting from the deletion of certain regions of the virus genome dispensable for virus growth, e.g., E3, deletions of regions whose function is restored in trans from a packaging cell line, e.g., E1, and its complementation by 293 cells (Graham, F. L., J. Gen. Virol. 36:59-72, 1977), as well as the upper limit for optimal packaging which is about 105%-108% of wild-type length.

The GEOS system can be used to generate a combinatorial library of adenoviral vectors with the goal of selecting those variants which selectively infect smooth muscle cells and/or selectively express a recombinant gene in smooth muscle cells. Such vector libraries can be derived by the GEOS method by combination of libraries of such nucleic acid components as (i) transcriptional regulatory sequence, which may be further broken down into sub-categories of promoters and enhancers, (ii) variants of viral early genes such as E1, E2, E3, E4, and MLP-L1, including loss-of-function mutants and deletions, and (iii) other adenoviral sequences which give rise to the various Ad subtypes (over 40 adenoviral subtypes have been isolated from humans).

In other embodiments, the subject GEOS method is used to optimize the therapeutic gene which is to be delivered by the gene therapy vector. For instance, secretion or cellular localization of a therapeutic protein can optimized, as appropriate, by the subject method.

ii) GEOS Recombination of Protein Domains

In one aspect, a goal of the present combinatorial method is to increase the number of novel genes and gene products that can be created by "domain shuffling" in a reasonable period of time. As described herein, polypeptide domains can be a polypeptide sequences derived from naturally occurring proteins, or can be artificial in sequence. In certain embodiments, the domain can be a nucleic acid sequences of other function, such as a sequence derived from a ribozyme. By accelerated molecular evolution through shuffling of such domains, a far greater population of novel gene products can be generated and screened in a meaningful period of time.

In one embodiment, the field of application of the present combinatorial method is in the generation of novel enzymatic activities, such as proteolytic enzymes. For example, combinatorial domain-shuffling can be used to rapidly generate a library of potential thrombolytic agents by randomly shuffling the domains of several known blood serum proteins. In another embodiment, the domain-shuffling technique can be used to generate a library of antibodies from which antibodies of particular affinity for a given antigen can be isolated. As described below, such an application can also be especially useful in grafting CDRs from one variable region to another, as required in the "humanization" of non-human antibodies. Similarly, the present technology can be extended to the immunoglobulin-super family, including the T-cell receptor, etc., to generate novel immulogically active proteins.

In another illustrative embodiment, the present domain-shuffling method can be used to generate novel signal-transduction proteins which can subsequently be used to generate cells which have altered responses to certain biological ligands or stimuli. For instance, protein tyrosine kinases play an important role in the control of cell growth and differentiation. Ligand binding to the extracellular domain of receptor tyrosine kinases often provides an important regulatory step which determines the selectivity of intracellular signaling pathways. Combinatorial domain-shuffling can be used to shuffle, for example, intracellular domains of receptor molecules or signal transduction proteins, including SH2 domains, SH3 domains, kinase domains, phosphatase domains, and phospholipase domains. In another embodiment, variant of SH2 and SH3 domains are randomly shuffled with domains engineered as either protein kinase or phosphatase inhibitors and the combinatorial polypeptide library screened for the ability to block the function of, for example, the action of oncogenic proteins such as sic or ras.

Many techniques are known in the art for screening gene products of combinatorial libraries made by point mutations, and for screening cDNA libraries for gene products having a certain property. Such techniques will be generally applicable to screening the gene libraries generated by the present domain-shuffling methodology. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose producted was detected. For instance, in the case of shuffling intracellular domains, phenotypic changes can be detected and used to isolate cells expressing a combinatorially-derived gene product conferring the new phenotype. Likewise, interaction trap assays can be used in vivo to screen large polypeptide libraries for proteins able to bind a "bait" protein, or alternatively, to inhibit binding of two proteins.

The domain shuffling methods described herein can be used to create new ribozymes. For ribozymes, one illustrative embodiment comprises screening a ribozyme library for the ability of molecules to cleave an mRNA molecule and disrupt expression of a protein in such a manner as to confer some phenotypic change to the cell.

In another embodiment, the subject GEOS method can be used to generate libraries of composite transcription factors, e.g., which are chimeric combinations of DNA binding domains and activation domains. Such composite factors can be optimized for, e.g., conditional sensitivity (inducibility or repressibility), level of expression when activated, cell-type specifity of expression, recognition of unique transcriptional regulatory elements, recruitment of basal and non-basal transcriptional complexes, and the like. Such composite factors may be useful in gene therapy, plant engineering, recombinant protein production and general research.

Nuclear localization signals, for example, have been shown to facilitate efficient nuclear localization of macromolecules. In order to facilitate nuclear import of an exogenous therapeutic DNA construct, peptide nuclear localization signals can be joined to a GEOS vector assembly by utilizing techniques for the covalent attachment of cationic peptides to double stranded DNA with a chemical cross-linker, resulting in a significant increase in nuclear uptake of the resulting construct (see e.g. Wolff, et al. (1998) Biotechnology 16: 80-85). Indeed, solid phase synthesis of a gene therapeutic construct using GEOS methodology could be directly followed with coupling to an appropriate cationic peptide nuclear localization signal allowing direct synthesis of the DNA therapeutic agent without an intermediate amplification step.

In yet another screening assay, the gene product, especially if its a polypeptide, is displayed on the surface of a cell or viral particle, and the ability of particular cells or viral particles to bind another molecule via this gene product is detected in a "panning assay". For example, the gene library can be cloned into the gene for a surface membrane protein of a bacterial cell, and the resulting fusion protein detected on the surface of the bacteria (Ladner et al., WO 88/06630; Fuchs et al. (1991) Bio/Technology 9:1370-1371; and Goward et al. (1992) TIBS 18:136-140). In another embodiment, gene library is expressed as fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage encodes the gene product on its surface, if a particular phage is recovered from an affinity matrix in low yield, the phage can be amplified by another round of infection. The group of almost identical E.coli filamentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) J. Biol. Chem. 267:16007-16010; Griffths et al. (1993) EMBO J 12:725-734; Clackson et al. (1991) Nature 352:624-628; and Barbas et al. (1992) PNAS 89:4457-4461).

a) Antibody Repertoires

Mouse monoclonal antibodies are readily generated by the fusion of antibody-producing B lymphocytes with myeloma cells. However, for therapeutic applications, human monoclonal antibodies are preferred. Despite extensive efforts, including production of heterohybridomas, Epstein-Barr virus immortalization of human B cells, and "humanization" of mouse antibodies, no general method comparable to the Kohler-Milstein approach has emerged for the generation of human monoclonal antibodies.

Recently, however, techniques have been developed for the generation of antibody libraries in E. coli capable of expressing the antigen binding portions of immunoglobulin heavy and light chains. For example, recombinant antibodies have been generated in the form of fusion proteins containing membrane proteins such as peptidoglycan-associated lipoprotein (PAL), as well as fusion proteins with the capsular proteins of viral particles, or simply as secreted proteins which are able to cross the bacterial membrane after the addition of a bacterial leader sequence at their N-termini. (See, for example, Fuchs et al. (1991) Bio/Technology 9:1370-1372; Bettes et al. (1988) Science 240:1041-1043; Skerra et al. (1988) Science 240:1038-1041; Hay et al. (1992) Hum. Antibod. Hybridomas 3:81-85; and Barbas et al. International Publication No. WO92/18019).

The display of antibody fragments on the surface of filamentous phage that encode the antibody gene, and the selection of phage binding to a particular antigen, offer a powerful means of generating specific antibodies in vitro. Typically, phage antibodies (phAbs) have been generated and expressed in bacteria by cloning repertoires of rearranged heavy and light chain V-genes into filamentous bacteriophage. Antibodies of a particular specificity can be selected from the phAb library by panning with antigen.

The present combinatorial approach can be applied advantageously to the production of recombinant antibodies by providing antibody libraries not readily accessible by any prior technique. For instance, in contrast to merely sampling combinations of $V_H$ and $V_L$ chains, the present method allows the complementarity-determining regions (CDRs) and framework regions (FRs) themselves to be randomly shuffled in order to create novel $V_H$ and $V_L$ regions which were not represented in the originally cloned rearranged V-genes.

Antibody variable domains consist of a β-sheet framework with three loops of hypervariable sequences (e.g. the CDRs), and the antigen binding site is shaped by loops from both heavy ($V_H$) and light ($V_L$) domains. The loops create antigen binding sites of a variety of shapes, ranging from flat surfaces to pockets. For human $V_H$ domains, the sequence diversity of the first two CDRs are encoded by a repertoire of about 50 germline $V_H$ segments (Tomlinson et al. (1992) J. Mol. Biol. 227:). The third CDR is generated from the combination of these segments with about 30 D and six J segments (Ichihara et al. (1988) EMBO J 7: 4141-4150). The lengths of the first two CDRs are restricted, with the length being 6 amino acid residues for CDR1, 17 residues, and for CDR2. However, the length of CDR3 can differ significantly, with lengths ranging from 4 to 25 residues.

For human light chain variable domains, the sequence diversity of the first two CDRs and part of CDR3 are encoded by a repertoire of about 50 human $V_\kappa$ segments (Meindl et al. (1990) Eur. J. Immunol. 20: 1855-1863) and >10 $V_\lambda$ segments (Chuchana et al. (1990) Eur. J. Immunol. 20: 1317-1325; and Combriato et al. (1991) Eur. J. Immunol. 21: 1513-1522). The lengths of the CDRs are as follows, CDR1=11-14 residues; CDR2=8 residues; and CDR3 ranges from 6 to 10 residues for $V_\kappa$ genes and 9 to 13 for $V_\lambda$ genes.

The present invention contemplates combinatorial methods for generating diverse antibody libraries, as well as reagents and kits for carrying out such methods. In one embodiment, the present combinatorial approach can be used to recombine both the framework regions and CDRs to generate a library of novel heavy and light chains. In another embodiment, domain-shuffling can be used to shuffle only the framework regions which flank specific CDR sequences. While both schemes can be used to generate antibodies directed to a certain antigen, the later strategy is particularly amenable to being used for "humanizing" non-human monoclonal antibodies.

In one embodiment, the combinatorial units useful for generating diverse antibody repertoires by the present domain-shuffling methods comprise exon constructs corresponding to fragments of various immunoglobulin variable regions flanked by intronic sequences that can drive their ligation. For example, the "exonic" sequences of the combinatorial units can be selected to encode essentially just a framework region or CDR; or can be generated to correspond to larger fragments which may include both CDR and FR sequences. The combinatorial units can be made by standard cloning techniques that manipulate DNA sequences into vectors which provide appropriate flanking intron fragments with non-palindromic overhangs.

Methods are generally known for directly obtaining the DNA sequence of the variable regions of any immunoglobulin chain by using a mixture of oligomer primers and PCR. For instance, mixed oligonucleotide primers corresponding to the 5' leader (signal peptide) sequences and/or FR1 sequences and a conserved 3' constant region primer have been used for PCR amplification of the heavy and light chain variable regions from a number of human antibodies directed to, for example, epitopes on HIV-I (gp 120, gp 42), digoxin, tetanus, immunoglobulins (rheumatoid factor), and MHC class I and II proteins (Larrick et al. (1991) *Methods: Companion to Methods in Enzymology* 2: 106-110). A similar strategy has also been used to amplify mouse heavy and light chain variable regions from murine antibodies, such as antibodies raised against human T cell antigens (CD3, CD6), carcino embryonic antigen, and fibrin (Larrick et al. (1991) *Bio Techniques* 11: 152-156).

In the present invention, RNA is isolated from mature B cells of, for example, peripheral blood cells, bone marrow, or spleen preparations, using standard protocols. First-strand cDNA is synthesized using primers specific for the constant region of the heavy chain(s) and each of the κ and λ light chains. Using variable region PCR primers, such as those shown in Table II below, the variable regions of both heavy and light chains are amplified (preferably in separate reactions) and ligated into appropriate expression vectors. The resulting libraries of vectors (e.g. one for each of the heavy and light chains) contain a variegated population of variable regions. The intronic addition can be carried out simultaneously for all three FR/CDR boundaries, or at fewer than all three boundaries. So, for example, leader-FR1(IVS 1-4), (IVS 5,6)CDR1, FR2(IVS 1-4), (IVS 5,6)CDR2, FR3(IVS 14) and (IVS 5,6)CDR3, FR4 combinatorial units can be generated with flanking non-palindromic overhangs.

TABLE II

Human Immunoglobulin Variable Region PCR Primers

5' End Sense

Human heavy chains
Group A
5'-GGGAATTCATGGACTGGACCTGGAGG(AG)TC(CT)-TCT(GT)C-3'

Group B
5'-GGGAATTCATGGAG(CT)TTGGGCTGA(CG)CTGG(CG)-TTTT-3'

Group C
5'-GGGAATTCATG(AG)A(AC)(AC)(AT)ACT(GT)TG(GT)-(AT)(CG)C(AT)(CT)(CG)CT(CT)CTG-3'

Human κ light chain
5'-GGGAATTCATGGACATG(AG)(AG)(AG)(AGT)(CT)CC-(ACT)(ACG)G(CT)GT)CA(CG)CTT-3'

Human λ light chain
5'-GGGAATTCATG(AG)CCTG(CG)(AT)C(CT)CCTCTC(CT)-T(CT)CT(CG)(AT)(CT)C-3'

3' End sense constant region

Human IgM heavy chain
5'-CCAAGCTTAGACGAGGGGGAAAAGGGTT-3'

Human IgG1 heavy chain
5'-CCAAGCTTGGAGGAGGGTGCCAGGGGG-3'

Human λ light chain
5'-CCAAGCTTGAAGCTCCTCAGAGGAGGG-3'

Human κ light chain
5'-CCAAGCTTTCATCAGATGGCGGGAAGAT-3'

TABLE II-continued

Murine Immunoglobulin Variable Region PCR Primers

5' End sense

Leader (signal peptide) region (amino acids -20 to -13)
Group A
5'-GGGGAATTCATG(GA)A(GC)TT(GC)(TG)GG(TC)T(AC)-A(AG)CT(GT)G(GA)TT-3'

Group B
5'-GGGGAATTCATG(GA)AATG(GC)A(GC)CTGGGT(CT)-(TA)T(TC)CTCT-3'

Framework I region (amino acids 1 to 8)
5'-GGGGAATTC(CG)AGGTG(CA)AGCTC(CG)(AT)(AG)(CG)-A(AG)(CT)C(CG)GGG-3'

3' End sense constant region
Mouse γ constant region (amino acids 121 to 131)
5'-GGAAGCTTA(TC)CTCCACACACAGG(AG)(AG)CCAGTG-GATAGAC-3'

Mouse κ light chain (amino acids 116 to 122)
5'-GGAAGCTTACTGGATGGTGGGAAGATGGA-3'

Bases in parentheses represent substitutions at a given residue. EcoRI and HindIII sites are underlined.

Optionally, the leader-FR1 (IVS 1-4) construct can be linked to an insoluble resin by standard techniques, and each set of combinatorial units (CDR1/FR2, CDR2/FR3, CDR3/FR4) can be sequentially annealed to the resin-bound nucleic acid with unbound reactants washed away between each round of addition. After addition of the (IVS 5,6)CDR3, FR4 units to the resin bound molecules, the resulting trans-spliced molecule can be released from the resin, PCR amplified using primers for the leader sequence and constant region, and subsequently cloned into an appropriate vector for generating a screenable population of antibody molecules.

Taking the dissection of the variable regions one step further, a set of domain libraries can be generated for ordered combinatorial ligation much the same as above, except that each combinatorial unit is flanked at its 5' end with a non-palindromic overhang sequence that is unable to drive a domain-shuffling reaction with the non-palindromic overhang sequence at its 3' end. With regard to ordered gene assembly, each combinatorial unit is effectively protected from addition by another unit having identical flanking intron fragments.

Furthermore, CDR combinatorial units can be generated which are completely random in sequence, rather than cloned from any antibody source. For example, a degenerate oligonucleotide can be synthesized for CDR1 which encodes all possible amino acid combinations for the 6 a.a. sequence. The nucleotide sequences which flank the CDR-encoding portion of the oligonucleotide comprise the flanking intron sequences and non-palindromic overhang sequences necessary to allow annealing of the degenerate oligonucleotide into the plasmid and reconstitute a construct which would produce a spliceable transcript. To avoid creation of stop codons which can result when codons are randomly synthesized using nucleotide monomers, "dirty bottle" synthesis can instead be carried out using a set of nucleotide trimers which encode all 20 amino acids.

With slight modification, the present ordered combinatorial ligation can be used to efficiently humanize monoclonal antibodies of non-human origin. The CDRs from the monoclonal antibody can be recombined with human framework region libraries (e.g. an FR1 library, an FR2 library, etc.) to produce a combinatorial population of variable regions in which the CDR sequences are held constant, but each of the framework regions have been randomized. The variable regions can be subsequently fused with sequences corresponding to the appropriate human constant regions, and the antibodies resulting from heavy and light chain association can be screened for antigen binding using standard panning assays such as phage display. In contrast to contemporary humanization schemes which require the practitioner to prejudicially choose a particular human scaffold into which the CDRs are grafted, the present technique provides a greater flexibility in choosing appropriate human framework regions which do not adversely affect antigen binding by the resultant chimeric antibody.

To illustrate, the variable regions of both the heavy and light chains of a mouse monoclonal antibody can be cloned using primers as described above. The sequence of each CDR can be obtained by standard techniques. The CDRs can be cloned into vectors which provide appropriate flanking intronic sequences and non-palindromic overhang sequences. As described above, the particular intronic fragments provided with each murine CDR and each human FR construct can be selected to disfavor multiple ligations at each step of addition to a resin bound nucleic acid. The library of human heavy chain leader, FR1(IVS-1-4) constructs can be immobilized on a resin, and in a first round of ligation, the heavy chain murine (IVS-5,6) CDR1 (IVS-1-4) construct is added under conditions which facilitate annealing of the overhang sequences. Un-ligated combinatorial units are washed away, and the library of human heavy chain (IVS-5,6) FR2 (IVS-1-4) units are admixed and ligated to the resin-bound nucleic acids terminating with the murine CDR construct. This process is carried out for the remaining murine CDR and human FR units of the heavy chain, and a similar process is used to construct combinatorial light chain chimeras as well. The resulting chimeric heavy and light chains can be cloned into a phage display library, and the phAbs screened in a panning assay to isolate humanized antibodies (and their genes) which bind the antigen of interest.

b) Combinatorial Enzyme Libraries

The subject method can also be used to generate novel enzymatic activities. In one embodiment, the subject combinatorial method can be used to generate novel blood-clotting or anticoagulant enzymes. Plasminogen activators (PAs) are a class of serine proteases that convert the proenzyme plasminogen into plasmin, which then degrades the fibrin network of blood clots. The plasminogen activators have been classified into two immunologically unrelated groups, the urokinase-type PAs (u-PA) and the tissue-type PA (tPA), with the later activator being the physiological vascular activator. These proteins, as well as other proteases of the fibrinolytic pathway, are composed of multiple structural domains which appear to have evolved by genetic assembly of individual domains with specific structural and/or functional properties. For instance, the amino terminal region of tPA is composed of multiple structural/functional domains found in other plasma proteins, including a "finger-like domain" homologous to the finger domains of fibronectin, an "epidermal growth factor domain" homologous to human EGF, and two disulfide-bonded triple loop structures, commonly referred to as "kringle domains", homologous to the kringle regions in plasminogen. The region comprising residues 276-527 (the "catalytic domain" is homologous to that of other serine proteases and contains the catalytic triad. In addition, the gene for tPA encodes a signal secretion peptide which directs secretion of the protein into the extracellular environment, as well as a pro-sequence which is cleaved from the inactive form of the protease (the "plasminogen") to active tPA during the fibrinolytic cascade.

These distinct domains in tPA are involved in several functions of the enzyme, including its binding to fibrin, stimulation of plasminogen activation by fibrin, and rapid in vivo clearance. Approaches used to characterize the functional contribution of these structural domains include isolation of independent structural domains as well as the production of variant proteins which lack one or more domains. For example, the fibrin selectivity of tPA is found to be mediated by its affinity for fibrin conferred by the finger-like domain and by at least one of the kringle domains.

The present combinatorial method can be used to generate novel plasminogen activators having superior thrombolytic properties, by generating a library of proteins through shuffling of the domains of plasma proteins. As described below, one mode of generating the combinatorial library comprises the random domain-shuffling of a mixture of coding sequences corresponding to each of the domains of the mature tPA protein. Briefly, a cDNA clone of tPA is obtained and, through the use of specific PCR amplimers, each of the 5 protein domains is amplified and isolated. Each of these amplified domains is then separately cloned into a plasmid as an exon module such that the 5' end of the exon is preceded by group II domains V-VI, and the 3' end of the exon is followed by group II domains I-III. Generation of style-stranded non-palindromic overhangs, and mixture of these constructs under annealing conditions, can result in random ligation of the exons to one and other and assembly of the combinatorial gene library which can subsequently be screened for fibrinolytic activity.

Moreover, combinatorial units can be generated from other proteins, including proteins having no catalytic role in blood clotting or fibrinolysis. For example, a library of catalytic domains can be generated from other thrombolytic proteases, blood clotting factors, and other proteases having peptidic activity similar to the typsin-like activity of tPA. Likewise, libraries of splicing constructs can be derived from EGF-like domains, finger-like domains, kringle domains, and Calcium-binding domains from a vast array of proteins which contain such moieties.

iii) GEOS-mediated Generation of Nucleic Acid Vaccines

Modern vaccine technology allows for the stimulation of antibodies to a given antigen by direct administration of a nucleic acid construct encoding that antigen. The GEOS methodology is particularly suited to this application. In this application, the GEOS insert nucleic acid component corresponds to the antigen to which immunity is directed. There are at least three types of methods for producing DNA vaccines: DNA vaccines consisting of *E. Coli*—derived expression vectors encoding the antigen of interest; recombinant immunoglobulin molecules containing foreign epitopes grafted into complementarity-determining regions (CDRs) resulting in the formation of "antigenized antibodies" which can induce immune responses against these engineered epitopes; and a merging of the two approaches called somatic transgene immunization (STI—see, Zanetti, et al. (1997) Nature Biotechnology, 15: 876-86) whereby an immunoglobulin heavy chain containing heterologous antigenic epitopes engineered into one or more CDRs, followed by the interspleenic innoculation of the DNA construct using tissue specific promoter and enhancer elements.

Construction of DNA vaccine constructs is particularly suited to the method of the present invention due to the flexibility of being able to interchange specific components in the discovery process. For example, when applied to the somatic transgene immunization method, the GEOS methodology allows for the rapid assembly and systematic variation of the critical STI DNA vaccine vectors components. These include: a general component for the expression vector backbone, components corresponding to frame-work regions (FRs), components corresponding to complementarity-determining regions (CDRs), components corresponding to tissue-specific immunoglobulin promoter and/or enhancer elements, and one or more antigenic epitope components to be inserted into any one or more of the CDR domains. A particular advantage of the invention in this application is the ability to vary: the CDR domain into which the immunogenic peptide fragment is to be substituted (i.e. CDR1, 2 or 3), the immunoglobulin chain into which the immunogenic peptide fragment is to be substituted (light chain or heavy chain), the number of CDR/immunogenic peptide fragment substitutions (from 1 to 3 per chain), and the tissue tropism of the resulting construct (through variation of the enhancer element component). Another advantage is that individual immunogenic peptide fragment elements can be assembled into the vector system as heterogeneous pools corresponding to different but related epitope families. Such "pooled vaccines" fund particular utility in stimulating antibodies which recognize highly variable regions of, for example, viral coat proteins.

GEOS components could also assist in immunoglobulin scaffold experiments where combinatorial arrays of scaffold sequences comprise at least one of the nucleic acid components. The ability to carry out multiplex experiments in which candidate scaffold components are combined with selected epitope candidates would allow for the generation of very large numbers of constructs from relatively few components. Furthermore the flexibility in vector assembly afforded by the GEOS methodology would allow one to switch rapidly between a phage display immunoglobulin system (which can undergo rapid selection processes for high-affinity epitope recognition) and a corresponding GEOS DNA vaccine construct.

iv) Two-hybrid Systems

The various yeast and mammalian two-hybrid systems allow for the rapid cloning and characterization of interacting polypeptides which are expressed as "bait" and "prey" constructs. The bait construct typically comprises a DNA binding domain element and a first "gene of interest" element which are fused in-frame. The prey construct typically comprises a transcriptional activation domain and a second "gene of interest" element which are fused in-frame. "Global grids" corresponding to all possible combination of multiple genes of interest can be used to investigate the association of various proteins in a biological system. The two-hybrid system allows the investigator to determine which genes encode proteins which interact with one another. Although standard cloning techniques are suitable for two-hybrid analysis of relatively small genetic systems, they are not efficient for the analysis of large genetic systems. The GEOS methodology, through delivery of heterogeneous pools comprising multiple "gene of interest" nucleic acid components, is particularly well suited to the systematic synthesis of two-hybrid bait and prey vectors from large numbers of pooled cDNAs. Such a pooled vector assemble strategy would be particularly useful in analyzing the huge number of novel cDNAs being recovered in human and mouse genome sequencing efforts. The GEOS vector assembly methodology provides a facile means for characterizing large numbers of cDNAs for potential biological interaction of their encoded products, thereby providing an initial biological characterization of these genes into related, biologically-interacting families.

v) Biosynthesis

Metabolic engineering can be used to alter organisms to optimize the production of practically any metabolic intermediate, including antibiotics, vitamins, amino acids such as phenylalanine and aromatic amino acids, ethanol, butanol, polymers such as xanthan gum and bacterial cellulose, peptides, and lipids. When such compounds are already produced by a host, the subject recombination techniques described herein can be used to optimize production of the desired metabolic intermediate, including such features as increasing enzyme substrate specificity and turnover number, altering metabolic fluxes to reduce the concentrations of toxic substrates or intermediates, increasing resistance of the host to such toxic compounds, eliminating, reducing or altering the need for inducers of gene expression/activity, increasing the production of enzymes necessary for metabolism, etc.

Enzymes can also be evolved for improved activity in solvents other than water. This is useful because intermediates in chemical syntheses are often protected by blocking groups which dramatically affect the solubility of the compound in aqueous solvents. Many compounds can be produced by a combination of pure chemical and enzymically catalyzed reactions. Performing enzymic reactions on almost insoluble substrates is clearly very inefficient, so the availability of enzymes that are active in other solvents will be of great use. One example of such a scheme is the evolution of a paranitrobenzyl esterase to remove protecting groups from an intermediate in loracarbef synthesis (Moore, J. C. and Arnold, F. H. Nature Biotechnology 14:458-467 (1996)). In this case alternating rounds of error-prone PCR and colony screening for production of a fluorescent reporter from a substrate analogue were used to generate a mutant esterase that was 16-fold more active than the parent molecule in 30% dimethylformamide. No individual mutation was found to contribute more than a 2-fold increase in activity, but it was the combination of a number of mutations which led to the overall increase. Structural analysis of the mutant protein showed that the amino acid changes were distributed throughout the length of the protein in a manner that could not have been rationally predicted. Sequential rounds of error-prone PCR have the problem that after each round all but one mutant is discarded, with a concomitant loss of information contained in all the other beneficial mutations. The subject GEOS recombination method avoids this problem, and would thus be ideally suited to evolving enzymes for catalysis in other solvents, as well as in conditions where salt concentrations or pH were different from the original enzyme optimas.

In addition, the yield of almost any metabolic pathway can be increased, whether consisting entirely of genes endogenous to the host organisms or all or partly heterologous genes. Optimization of the expression levels of the enzymes in a pathway is more complex than simply maximizing expression. In some cases regulation, rather than constitutive expression of an enzyme may be advantageous for cell growth and therefore for product yield, as seen for production of phenylalanine (Backman et al. Ann. NY Acad. Sci. 589:16-24 (1990)) and 2-keto-L-gluconic acid (Anderson et al. U.S. Pat. No. 5,032,514). In addition, it is often advantageous for industrial purposes to express proteins in organisms other than their original hosts. New host strains may be preferable for a variety of reasons, including ease of cloning and transformation, pathogenicity, ability to survive in particular environments and a knowledge of the physiology and genetics of the organisms. However, proteins expressed in heterologous organisms often show markedly reduced activity for a variety of reasons including inability to fold properly in the new host (Sarthy et al. Appl. Environ. Micro. 53:1996-2000 (1987)). Such difficulties can indeed be overcome by the recombination strategies of the instant invention.

a. Antibiotics

The range of natural small molecule antibiotics includes but is not limited to peptides, peptidolactones, thiopeptides, beta-lactams, glycopeptides, lantibiotics, microcins, polyketide-derived antibiotics (anthracyclins, tetracyclins, macrolides, avermectins, polyethers and ansamycins), chloramphenicol, aminoglycosides, aminocyclitols, polyoxins, agrocins and isoprenoids.

There are at least three ways in which the GEOS recombination techniques of the instant invention can be used to facilitate novel drug synthesis, or to improve biosynthesis of existing antibiotics.

First, antibiotic synthesis enzymes can be "evolved" together with transport systems that allow entry of compounds used as antibiotic precursors to improve uptake and incorporation of function-altering artificial side chain precursors. For example, penicillin V is produced by feeding *Penicillium* the artificial side chain precursor phenoxyacetic acid, and LY146032 by feeding *Streptomyces roseosporus* decanoic acid (Hopwood, Phil. Trans. R. Soc. Lond. B 324: 549-562 (1989)). Poor precursor uptake and poor incorporation by the synthesizing enzyme often lead to inefficient formation of the desired product. The use of the subject recombination method on these two systems can increase the yield of desired product.

Furthermore, a combinatorial approach can be taken in which an enzyme is shuffled for novel catalytic activity/substrate recognition (perhaps by including randomizing oligonucleotides in key positions such as the active site). A number of different substrates (for example, analogues of side chains that are normally incorporated into the antibiotic) can then be tested in combination with all the different enzymes and tested for biological activity. In this embodiment, plates are made containing different potential antibiotic precursors (such as the side chain analogues). The microorganisms containing the shuffled library (the library strain) are replicated onto those plates, together with a competing, antibiotic sensitive, microorganism (the indicator strain). Library cells that are able to incorporate the new side chain to produce an effective antibiotic will thus be able to compete with the indicator strain, and will be selected for.

Second, the expression of heterologous genes transferred from one antibiotic synthesizing organism to another can be optimized. The newly introduced enzyme(s) act on secondary metabolites in the host cell, transforming them into new compounds with novel properties. Using traditional methods, introduction of foreign genes into antibiotic synthesizing hosts has already resulted in the production of novel hybrid antibiotics. Examples include mederrhodin, dihydrogranatirhodin, 6-deoxyerythromycin A, isovalerylspiramycin and other hybrid macrolides (Cameron et. al. Appl. Biochem. Biotechnol. 38:105-140 (1993)). The GEOS recombination techniques of the instant invention can be used to optimize expression of the foreign genes, to stabilize the enzyme in the new host cell, and to increase the activity of the introduced enzyme against its new substrates in the new host cell. In some embodiments of the invention, the host genome may also be so optimized.

Third, the substrate specificity of an enzyme involved in secondary metabolism can be altered so that it will act on and modify a new compound or so that its activity is changed and it acts at a different subset of positions of its normal substrate. GEOS recombination can be used to alter the substrate specificities of enzymes. Furthermore, in addition to GEOS recombination of individual enzymes being a strategy to generate novel antibiotics, GEOS recombination of entire pathways, by altering enzyme ratios, will alter metabolite fluxes and may result, not only in increased antibiotic synthesis, but also in the synthesis of different antibiotics. This can be deduced from the observation that expression of different genes from the same cluster in a foreign host leads to different products being formed (see p. 80 in Hutchinson et. al., (1991) Ann NY Acad Sci, 646:78-93). GEOS recombination of the introduced gene clusters may result in a variety of expression levels of different proteins within the cluster (because it produces different combinations of, in this case regulatory, mutations). This in turn may lead to a variety of different end products. Thus, "evolution" of an existing antibiotic synthesizing pathway could be used to generate novel antibiotics either by modifying the rates or substrate specificities of enzymes in that pathway.

Additionally, antibiotics can also be produced in vitro by the action of a purified enzyme on a precursor. For example isopenicillin N synthase catalyses the cyclization of many analogues of its normal substrate (d-(L-a-aminoadipyl)-L-cysteinyl-D-valine) (Hutchinson, Med. Res. Rev. 8:557-567 (1988)). Many of these products are active as antibiotics. A wide variety of substrate analogues can be tested for incorporation by secondary metabolite synthesizing enzymes without concern for the initial efficiency of the reaction. GEOS recombination can be used subsequently to increase the rate of reaction with a promising new substrate.

Thus, organisms already producing a desired antibiotic can be evolved with the GEOS recombination techniques described herein to maximize production of that antibiotic. Additionally, new antibiotics can be evolved by manipulation of genetic material from the host by the GEOS recombination techniques described herein. Genes for antibiotic production can be transferred to a preferred host after cycles of GEOS recombination. Antibiotic genes are generally clustered and are often positively regulated, making them especially attractive candidates for the GEOS recombination techniques of the instant invention. Additionally, some genes of related pathways show cross-hybridization, making them preferred candidates for the generation of new pathways for new antibiotics by the GEOS recombination techniques of the invention. Furthermore, increases in secondary metabolite production including enhancement of substrate fluxes (by increasing the rate of a rate limiting enzyme, deregulation of the pathway by suppression of negative control elements or over expression of activators and the relief of feedback controls by mutation of the regulated enzyme to a feedback-insensitive deregulated protein) can be achieved by GEOS recombination without exhaustive analysis of the regulatory mechanisms governing expression of the relevant gene clusters.

The host chosen for expression of evolved genes is preferably resistant to the antibiotic produced, although in some instances production methods can be designed so as to sacrifice host cells when the amount of antibiotic produced is commercially significant yet lethal to the host. Similarly, bioreactors can be designed so that the growth medium is continually replenished, thereby "drawing off" antibiotic produced and sparing the lives of the producing cells. Preferably, the mechanism of resistance is not the degradation of the antibiotic produced.

Numerous screening methods for increased antibiotic expression are known in the art, as discussed above, including screening for organisms that are more resistant to the antibiotic that they produce. This may result from linkage between expression of the antibiotic synthesis and antibiotic resistance genes (Chater, Bio/Technology 8:115-121 (1990)). Another screening method is to fuse a reporter gene (e.g. xylE from the Pseudomonas TOL plasmid) to the antibiotic production genes. Antibiotic synthesis gene expression can then be measured by looking for expression of the reporter (e.g. xylE encodes a catechol dioxygenase which produces yellow muconic semialdehyde when colonies are sprayed with catechol (Zukowski et al. Proc. Natl. Acad. Sci. U.S.A. 80:1101-1105 (1983)).

The wide variety of cloned antibiotic genes provides a wealth of starting materials for the GEOS recombination techniques of the instant invention. For example, genes have been cloned from *Streptomyces cattleya* which direct cephamycin C synthesis in the non-antibiotic producer *Streptomyces lividans* (Chen et al. Bio/Technology 6:1222-1224 (1988)). Clustered genes for penicillin biosynthesis (delta-(L-alpha-aminoadipyl)-L-cysteinyl-D-valine synthetase; isopenicillin N synthetase and acyl coenzyme A:6-aminopenicillanic acid acyltransferase) have been cloned from *Penicillium chrysogenum*. Transfer of these genes into *Neurospora crassa* and *Aspergillus niger* result in the synthesis of active penicillin V (Smith et al. Bio/Technology 8:39-41 (1990)). For a review of cloned genes involved in Cephalosporin C, Penicillins G and V and Cephamycin C biosynthesis, see Piepersberg, Crit. Rev. Biotechnol. 14:251-285 (1994). For a review of cloned clusters of antibiotic-producing genes, see Chater Bio/Technology 8:115-121 (1990). Other examples of antibiotic synthesis genes transferred to industrial producing strains, or over expression of genes, include tylosin, cephamycin C, cephalosporin C, LL-E33288 complex (an antitumor and antibacterial agent), doxorubicin, spiramycin and other macrolide antibiotics, reviewed in Cameron et al. Appl. Biochem. Biotechnol. 38:105-140 (1993).

b. Biosynthesis to Replace Chemical Synthesis of Antibiotics

Some antibiotics are currently made by chemical modifications of biologically produced starting compounds. Complete biosynthesis of the desired molecules may currently be impractical because of the lack of an enzyme with the required enzymatic activity and substrate specificity. For example, 7-aminodeacetooxycephalosporanic acid (7-ADCA) is a precursor for semi-synthetically produced cephalosporins. 7-ADCA is made by a chemical ring expansion from penicillin V followed by enzymatic deacylation of the phenoxyacetal group. Cephalosporin V could in principle be produced biologically from penicillin V using penicillin N expandase, but penicillin V is not used as a substrate by any known expandase. The GEOS recombination techniques of the invention can be used to alter the enzyme so that it will use penicillin V as a substrate. Similarly, penicillin transacylase could be so modified to accept cephalosporins or cephamycins as substrates.

In yet another example, penicillin amidase expressed in *E. coli* is a key enzyme in the production of penicillin G derivatives. The enzyme is generated from a precursor peptide and tends to accumulate as insoluble aggregates in the periplasm unless non-metabolizable sugars are present in the medium (Scherrer et al. Appl. Microbiol. Biotechnol. 42:85-91 (1994)). Evolution of this enzyme through the methods of the instant invention could be used to generate an enzyme that folds better, leading to a higher level of active enzyme expression.

In yet another example, Penicillin G acylase covalently linked to agarose is used in the synthesis of penicillin G derivatives. The enzyme can be stabilized for increased activity, longevity and/or thermal stability by chemical modification (Fernandez-Lafuente et. al. Enzyme Microb. Technol. 14:489-495 (1992). Increased thermal stability is an especially attractive application of the GEOS recombination techniques of the instant invention, which can obviate the need for the chemical modification of such enzymes. Selection for thermostability can be performed in vivo in *E. coli* or in thermophiles at higher temperatures. In general, thermostability is a good first step in enhancing general stabilization of enzymes.

c. Polyketides

Polyketides include antibiotics such as tetracycline and erythromycin, anti-cancer agents such as daunomycin, immunosuppressants such as FK506 and rapamycin and veterinary products such as monesin and avermectin. Polyketide synthases (PKS's) are multifunctional enzymes that control the chain length, choice of chain-building units and reductive cycle that generates the huge variation in naturally occurring polyketides. Polyketides are built up by sequential transfers of "extender units" (fatty acyl CoA groups) onto the appropriate starter unit (examples are acetate, coumarate, propionate and malonamide). The PKS's determine the number of condensation reactions and the type of extender groups added and may also fold and cyclize the polyketide precursor. PKS's reduce specific beta-keto groups and may dehydrate the resultant beta-hydroxyls to form double bonds. Modifications of the nature or number of building blocks used, positions at which beta-keto groups are reduced, the extent of reduction and different positions of possible cyclizations, result in formation of different final products. Polyketide research is currently focused on modification and inhibitor studies, site directed mutagenesis and 3-D structure elucidation to lay the groundwork for rational changes in enzymes that will lead to new polyketide products.

Recently, McDaniel et al. (Science 262:1546-1550 (1995)) have developed a *Streptomyces* host-vector system for efficient construction and expression of recombinant PKSs. Hutchinson (Bio/Technology 12:375-308 (1994)) reviewed targeted mutation of specific biosynthetic genes and suggested that microbial isolates can be screened by DNA hybridization for genes associated with known pharmacologically active agents so as to provide new metabolites and large amounts of old ones. In particular, that review focuses on polyketide synthase and pathways to aminoglycoside and oligopeptide antibiotics.

The GEOS recombination techniques of the instant invention can be used to generate modified enzymes and enzyme clusters that produce novel polyketides without such detailed analytical effort The availability of the PKS genes on plasmids and the existence of *E. coli-Streptomyces* shuttle vectors (Wehmeier Gene 165:149-150 (1995)) makes the process of GEOS recombination especially attractive by the techniques described herein. Techniques for selection of antibiotic producing organisms can be used as described herein; additionally, in some embodiments screening for a particular desired polyketide activity or compound is preferable.

d. Isoprenoids

Isoprenoids result from cyclization of farnesyl pyrophosphate by sesquiterpene synthases. The diversity of isoprenoids is generated not by the backbone, but by control of cyclization. Cloned examples of isoprenoid synthesis genes include trichodiene synthase from *Fusarium sprorotrichioides*, pentalene synthase from *Streptomyces*, aristolochene synthase from *Penicillium roquefortii*, and epi-aristolochene synthase from *N. tabacum* (Cane, D. E. (1995). Isoprenoid antibiotics, pages 633-655, in "Genetics and Biochemistry of Antibiotic Production" edited by Vining, L. C. & Stuttard, C., published by Butterworth-Heinemann). GEOS recombination of sesquiterpene synthases will be of use both in allowing expression of these enzymes in heterologous hosts (such as plants and industrial microbial strains) and in alteration of enzymes to change the cyclized product made. A large number of isoprenoids are active as antiviral, antibacterial, antifungal, herbicidal, insecticidal or cytostatic agents. Antibacterial and antifungal isoprenoids could thus be preferably screened for using the indicator cell type system described herein, with the producing cell competing with bacteria or fungi for nutrients. Antiviral isoprenoids could be screened for preferably by their ability to confer resistance to viral attack on the producing cell.

e. Bioactive Peptide Derivatives

Examples of bioactive non-ribosomally synthesized peptides include the antibiotics cyclosporin, pepstatin, actinomycin, gramicidin, depsipeptides, vancomycin, etc. These peptide derivatives are synthesized by complex enzymes rather than ribosomes. Again, increasing the yield of such non-ribosomally synthesized peptide antibiotics has thus far been done by genetic identification of biosynthetic "bottlenecks" and over expression of specific enzymes (See, for example, p. 133-135 in "Genetics and Biochemistry of Antibiotic Production" edited by Vining, L. C. & Stuttard, C., published by Butterworth-Heinemann). GEOS recombination of the enzyme clusters can be used to improve the yields of existing bioactive non-ribosomally made peptides in both natural and heterologous hosts. Like polyketide synthases, peptide synthases are modular and multifunctional enzymes catalyzing condensation reactions between activated building blocks (in this case amino acids) followed by modifications of those building blocks (see Kleinkauf, H. and von Dohren, H. Eur. J. Biochem. 236:335-351 (1996)). Thus, as for polyketide synthases, GEOS recombination can also be used to alter peptide synthases: modifying the specificity of the amino acid recognized by each binding site on the enzyme and altering the activity or substrate specificities of sites that modify these amino acids to produce novel compounds with antibiotic activity.

Other peptide antibiotics are made ribosomally and then post-translationally modified. Examples of this type of antibiotics are lantibiotics (produced by gram positive bacteria such Staphylococcus, Streptomyces, Bacillus, and Actinoplanes) and microcins (produced by Enterobacteriaceae). Modifications of the original peptide include (in lantibiotics) dehydration of serine and threonine, condensation of dehydroamino acids with cysteine, or simple N- and C-terminal blocking (microcins). For ribosomally made antibiotics both the peptide-encoding sequence and the modifying enzymes may have their expression levels modified by GEOS recombination. Again, this will lead to both increased levels of antibiotic synthesis, and by modulation of the levels of the modifying enzymes (and the sequence of the ribosomally synthesized peptide itself) novel antibiotics.

Screening can be done as for other antibiotics as described herein, including competition with a sensitive (or even initially insensitive) microbial species. Use of competing bacteria that have resistances to the antibiotic being produced will select strongly either for greatly elevated levels of that antibiotic (so that it swamps out the resistance mechanism) or for novel derivatives of that antibiotic that are not neutralized by the resistance mechanism.

f. Polymers

Several examples of metabolic engineering to produce biopolymers have been reported, including the production of the biodegradable plastic polyhydroxybutarate (PHB), and the polysaccharide xanthan gum. For a review, see Cameron et al. Applied Biochem. Biotech. 38:105-140 (1993). Genes for these pathways have been cloned, making them excellent candidates for the GEOS recombination techniques described herein. Expression of such evolved genes in a commercially viable host such as E. coli is an especially attractive application of this technology.

Examples of starting materials for GEOS recombination include but are not limited to genes from bacteria such as Alcaligenes, Zoogloea, Rhizobium, Bacillus, and Azobacter, which produce polyhydroxyalkanoates (PHAs) such as polyhyroxybutyrate (PHB) intracellularly as energy reserve materials in response to stress. Genes from Alcaligenes eutrophus that encode enzymes catalyzing the conversion of acetoacetyl CoA to PHB have been transferred both to E. coli and to the plant Arabidopsis thaliana (Poirier et al. Science 256:520-523 (1992)). Two of these genes (phbB and phbC, encoding acetoacetyl-CoA reductase and PHB synthase respectively) allow production of PHB in Arabidopsis. The plants producing the plastic are stunted, probably because of adverse interactions between the new metabolic pathway and the plants' original metabolism (i.e., depletion of substrate from the mevalonate pathway). Improved production of PHB in plants has been attempted by localization of the pathway enzymes to organelles such as plastids. Other strategies such as regulation of tissue specificity, expression timing and cellular localization have been suggested to solve the deleterious effects of PHB expression in plants. The GEOS recombination techniques of the invention can be used to modify such heterologous genes as well as specific cloned interacting pathways (e.g., mevalonate), and to optimize PHB synthesis in industrial microbial strains, for example to remove the requirement for stresses (such as nitrogen limitation) in growth conditions.

Additionally, other microbial polyesters are made by different bacteria in which additional monomers are incorporated into the polymer (Peoples et al. in Novel Biodegradable Microbial Polymers, E A Dawes, ed., pp 191-202 (1990)). Application of the subject GEOS recombination method to these genes or pathways singly or in combination into a heterologous host will allow the production of a variety of polymers with differing properties, including variation of the monomer subunit ratios in the polymer. Another polymer whose synthesis may be manipulated by GEOS recombination is cellulose. The genes for cellulose biosynthesis have been cloned from Agrobacterium tumefaciens (Matthysse, A. G. et. al. J. Bacteriol. 177:1069-1075 (1995)). GEOS recombination of this biosynthetic pathway could be used either to increase synthesis of cellulose, or to produce mutants in which alternative sugars are incorporated into the polymer.

g. Carotenoids

Carotenoids are a family of over 600 terpenoids produced in the general isoprenoid biosynthetic pathway by bacteria, fungi and plants (for a review, see Armstrong, J. Bact. 176: 4795-4802 (1994)). These pigments protect organisms against photooxidative damage as well as functioning as anti-tumor agents, free radical-scavenging anti-oxidants, and enhancers of the immune response. Additionally, they are used commercially in pigmentation of cultured fish and shellfish. Examples of carotenoids include but are not limited to myxobacton, spheroidene, spheroidenone, lutein, astaxanthin, violaxanthin, 4-ketorulene, myxoxanthrophyll, echinenone, lycopene, zeaxanthin and its mono- and di-glucosides, alpha-, beta-, gamma- and delta-carotene, beta-cryptoxanthin monoglucoside and neoxanthin.

Carotenoid synthesis is catalyzed by relatively small numbers of clustered genes: 11 different genes within 12 kb of DNA from Myxococcus xanthus (Botella et al. Eur. J. Biochem. 233:238-248 (1995)) and 8 genes within 9 kb of DNA from *Rhodobacter sphaeroides* (Lang et. al. J. Bact. 177: 2064-2073 (1995)). In some microorganisms, such as *Thermus thermophilus*, these genes are plasmid-borne (Tabata et al. FEBS Letts 341:251-255 (1994)). These features make carotenoid synthetic pathways especially attractive candidates for GEOS recombination.

Transfer of some carotenoid genes into heterologous organisms results in expression. For example, genes from *Erwina uredovora* and *Haematococcus pluvialis* will function together in *E. coli* (Kajiwara et al. Plant Mol. Biol. 29:343-352 (1995)). *E. herbicola* genes will function in *R. sphaeroides* (Hunter et al. J. Bact. 176:3692-3697 (1994)). However, some other genes do not; for example, *R. capsulatus* genes do not direct carotenoid synthesis in *E. coli* (Marrs, J. Bact. 146:1003-1012 (1981)).

In an embodiment of the invention, the GEOS recombination techniques of the invention can be used to generate variants in the regulatory and/or structural elements of genes in the carotenoid synthesis pathway, allowing increased expression in heterologous hosts. Indeed, traditional techniques have been used to increase carotenoid production by increasing expression of a rate limiting enzyme in *Thermus thermophilus* (Hoshino et al. Appl. Environ. Micro. 59:3150-3153 (1993)). Furthermore, mutation of regulatory genes can cause constitutive expression of carotenoid synthesis in actinomycetes, where carotenoid photoinducibility is otherwise unstable and lost at a relatively high frequency in some species (Kato et al. Mol. Gen. Genet. 247:387-390 (1995)). These are both mutations that can be obtained by GEOS recombination.

The GEOS recombination techniques of the invention as described herein can be used to evolve one or more carotenoid synthesis genes in a desired host without the need for analysis of regulatory mechanisms. Since carotenoids are colored, a calorimetric assay in microtiter plates, or even on growth media plates, can be used for screening for increased production.

In addition to increasing expression of carotenoids, carotenogenic biosynthetic pathways have the potential to produce a wide diversity of carotenoids, as the enzymes involved appear to be specific for the type of reaction they will catalyze, but not for the substrate that they modify. For example, two enzymes from the marine *bacterium Agrobacterium aurantiacum* (CrtW and CrtZ) synthesize six different ketocarotenoids from beta-carotene (Misawa et al. J. Bact. 177: 6576-6584 (1995)). This relaxed substrate specificity means that a diversity of substrates can be transformed into an even greater diversity of products. Introduction of foreign carotenoid genes into a cell can lead to novel and functional carotenoid-protein complexes, for example in photosynthetic complexes (Hunter et al. J. Bact. 176:3692-3697 (1994)). Thus, the deliberate recombination of enzymes through the GEOS recombination techniques of the invention is likely to generate novel compounds. Screening for such compounds can be accomplished, for example, by the cell competition/survival techniques discussed above and by a calorimetric assay for pigmented compounds.

Another method of identifying new compounds is to use standard analytical techniques such as mass spectroscopy, nuclear magnetic resonance, high performance liquid chromatography, etc. Recombinant microorganisms can be pooled and extracts or media supernatants assayed from these pools. Any positive pool can then be subdivided and the procedure repeated until the single positive is identified ("sib-selection").

h. Indigo Biosynthesis

Many dyes, i.e. agents for imparting color, are specialty chemicals with significant markets. As an example, indigo is currently produced chemically. However, nine genes have been combined in *E. coli* to allow the synthesis of indigo from glucose via the tryptophan/indole pathway (Murdock et al. Bio/Technology 11:381-386 (1993)). A number of manipulations were performed to optimize indigo synthesis: cloning of nine genes, modification of the fermentation medium and directed changes in two operons to increase reaction rates and catalytic activities of several enzymes. Nevertheless, bacterially produced indigo is not currently an economic proposition. The GEOS recombination techniques of the instant invention could be used to optimize indigo synthesizing enzyme expression levels and catalytic activities, leading to increased indigo production, thereby making the process commercially viable and reducing the environmental impact of indigo manufacture. Screening for increased indigo production can be done by calorimetric assays of cultures in microtiter plates.

i. Amino Acids

Amino acids of particular commercial importance include but are not limited to phenylalanine, monosodium glutamate, glycine, lysine, threonine, tryptophan and methionine. Backman et al. (Ann. NY Acad. Sci. 589:16-24 (1990)) disclosed the enhanced production of phenylalanine in *E. coli* via a systematic and downstream strategy covering organism selection, optimization of biosynthetic capacity, and development of fermentation and recovery processes.

As described in Simpson et al. (Biochem Soc Trans, 23:381-387 (1995)), current work in the field of amino acid production is focused on understanding the regulation of these pathways in great molecular detail. The GEOS recombination techniques of the instant invention would obviate the need for this analysis to obtain bacterial strains with higher secreted amino acid yields. Amino acid production could be optimized for expression using GEOS recombination of the amino acid synthesis and secretion genes as well as enzymes at the regulatory phosphoenolpyruvate branchpoint, from such organisms as *Serratia marcescens, Bacillus*, and the *Corynebacterium-Brevibacterium* group. In some embodiments of the invention, screening for enhanced production is preferably done in microtiter wells, using chemical tests well known in the art that are specific for the desired amino acid. Screening/selection for amino acid synthesis can also be done by using auxotrophic reporter cells that are themselves unable to synthesize the amino acid in question. If these reporter cells also produce a compound that stimulates the growth of the amino acid producer (this could be a growth factor, or even a different amino acid), then library cells that produce more amino acid will in turn receive more growth stimulant and will therefore grow more rapidly.

j. Vitamin C Synthesis

L-Ascorbic acid (vitamin C) is a commercially important vitamin with a world production of over 35,000 tons in 1984. Most vitamin C is currently manufactured chemically by the Reichstein process, although recently bacteria have been engineered that are able to transform glucose to 2,5-ketogluconic acid, and that product to 2-keto-L-idonic acid, the precursor to L-ascorbic acid (Boudrant, Enzyme Microb. Technol. 12:322-329 (1990)).

The efficiencies of these enzymatic steps in bacteria are currently low. Using the GEOS recombination techniques of the instant invention, the genes can be genetically engineered to create one or more operons followed by expression optimization of such a hybrid L-ascorbic acid synthetic pathway to result in commercially viable microbial vitamin C biosynthesis. In some embodiments, screening for enhanced L-ascorbic acid production is preferably done in microtiter plates, using assays well known in the art.

vi) Recombination of Genes for Bioremediation

Modern industry generates many pollutants for which the environment can no longer be considered an infinite sink. Naturally occurring microorganisms are able to metabolize thousands of organic compounds, including many not found in nature (e.g xenobiotics). Bioremediation, the deliberate use of microorganisms for the biodegradation of man-made wastes, is an emerging technology that offers cost and practicality advantages over traditional methods of disposal. The success of bioremediation depends on the availability of organisms that are able to detoxify or mineralize pollutants. Microorganisms capable of degrading specific pollutants can be generated by genetic engineering and GEOS recombination.

Although bioremediation is an aspect of pollution control, a more useful approach in the long term is one of prevention before industrial waste is pumped into the environment. Exposure of industrial waste streams to GEOS-generated microorganisms capable of degrading the pollutants they contain would result in detoxification of mineralization of these pollutants before the waste stream enters the environment. Issues of releasing recombinant organisms can be avoided by containing them within bioreactors fitted to the industrial effluent pipes. This approach would also allow the microbial mixture used to be adjusted to best degrade the particular wastes being produced. Finally, this method would avoid the problems of adapting to the outside world and dealing with competition that face many laboratory microorganisms.

In the wild, microorganisms have evolved new catabolic activities enabling them to exploit pollutants as nutrient sources for which there is no competition. However, pollutants that are present at low concentrations in the environment may not provide a sufficient advantage to stimulate the evolution of catabolic enzymes. For a review of such naturally occurring evolution of biodegradative pathways and the manipulation of some of microorganisms by classical techniques, see Ramos et al., Bio/Technology 12:1349-1355 (1994).

Generation of new catabolic enzymes or pathways for bioremediation has thus relied upon deliberate transfer of specific genes between organisms (Wackett et al., supra), forced matings between bacteria with specific catabolic capabilities (Brenner et al. Biodegradation 5:359-377 (1994)), or prolonged selection in a chemostat. Some researchers have attempted to facilitate evolution via naturally occurring genetic mechanisms in their chemostat selections by including microorganisms with a variety of catabolic pathways (Kellogg et. al. Science 214:1133-1135 (1981); Chakrabarty American Society of Micro. Biol. News 62:130-137 (1996)). For a review of efforts in this area, see Cameron et al. Applied Biochem. Biotech. 38:105-140 (1993).

Current efforts in improving organisms for bioremediation take a labor-intensive approach in which many parameters are optimized independently, including transcription efficiency from native and heterologous promoters, regulatory circuits and translational efficiency as well as improvement of protein stability and activity (Timmis et al. Ann. Rev. Microbiol. 48:525-527 (1994)).

A GEOS recombination approach overcomes a number of limitations in the bioremediation capabilities of naturally occurring microorganisms. Both enzyme activity and specificity can be altered, simultaneously or sequentially, by the methods of the invention. For example, novel catabolic enzymes can be created to increase the rate at which they act on a substrate. Although knowledge of a rate-limiting step in a metabolic pathway is not required to practice the invention, rate-limiting proteins in pathways can be evolved to have increased expression and/or activity, the requirement for inducing substances can be eliminated, and enzymes can be evolved that catalyze novel reactions.

Some examples of chemical targets for bioremediation include but are not limited to benzene, xylene, and toluene, camphor, naphthalene, halogenated hydrocarbons, polychlorinated biphenyls (PCBs), trichlorethylene, pesticides such as pentachlorophenyls (PCPs), and herbicides such as atrazine.

a) Aromatic Hydrocarbons

Preferably, when an enzyme is "evolved" to have a new catalytic function, that function is expressed, either constitutively or in response to the new substrate. The target recombination method subjects both structural and regulatory elements (including the structure of regulatory proteins) of a protein to recombinogenic mutagenesis simultaneously. Selection of mutants that are efficiently able to use the new substrate as a nutrient source will be sufficient to ensure that both the enzyme and its regulation are optimized, without detailed analysis of either protein structure or operon regulation.

Examples of aromatic hydrocarbons include but are not limited to benzene, xylene, toluene, biphenyl, and polycyclic aromatic hydrocarbons such as pyrene and naphthalene. These compounds are metabolized via catechol intermediates. Degradation of catechol by *Pseudomonas putida* requires induction of the catabolic operon by cis, cis-muconate which acts on the CatR regulatory protein. The binding site for the CatR protein is G-N11-A, while the optimal sequence for the LysR class of activators (of which CatR is a member) is T-N11-A. Mutation of the G to a T in the CatR binding site enhances the expression of catechol metabolizing genes (Chakrabarty, American Society of Microbiology News 62:130-137 (1996)). This demonstrates that the control of existing catabolic pathways is not optimized for the metabolism of specific xenobiotics, and suggests that the subject method can be used to generate recombinant bacteria that are better able to degrade the target compound.

As an example of starting materials, dioxygenases are required for many pathways in which aromatic compounds are catabolized. Even small differences in dioxygenase sequence can lead to significant differences in substrate specificity (Furukawa et al. J. Bact. 175:5224-5232 (1993); Erickson et al. App. Environ. Micro. 59:3858-3862 (1993)). A hybrid enzyme made using sequences derived from two or more "parental" enzymes may possess catalytic activities that are intermediate between the parents (Erickson, ibid.), or may actually be better than either parent for a specific reaction (Furukawa et al. *J. Bact.* 176:2121-2123 (1994)). For example, a four subunit enzyme can be produced by expressing two or more subunits from different dioxygenases. Thus, sequences from one or more genes encoding dioxygenases can be used in the recombination techniques of the instant invention, to generate enzymes with new specificities. In addition, other features of the catabolic pathway can also be evolved using these techniques, simultaneously or sequentially, to optimize the metabolic pathway for an activity of interest.

b) Halogenated Hydrocarbons

Large quantities of halogenated hydrocarbons are produced annually for uses as solvents and biocides. These include, in the United States alone, over 5 million tons of both 1,2-dichloroethane and vinyl chloride used in PVC production in the U.S. alone. The compounds are largely not biodegradable by processes in single organisms, although in principle haloaromatic catabolic pathways can be constructed by combining genes from different microorganisms. Enzymes can be manipulated to change their substrate specificities. The subject method offers the possibility of tailoring enzyme specificity to new substrates without needing detailed structural analysis of the enzymes.

As an example of possible starting materials for the methods of the instant invention, Wackett et al. (Nature 368:627-629 (1994)) recently demonstrated that through classical techniques a recombinant Pseudomonas strain in which seven genes encoding two multi-component oxygenases are combined, generated a single host that can metabolize polyhalogenated compounds by sequential reductive and oxidative techniques to yield non-toxic products. These and/or related materials can be subjected to the combinatorial techniques discussed above so as to evolve and optimize a biodegradative pathway in a single organism.

Trichloroethylene is a significant groundwater contaminant. It is degraded by microorganisms in a cometabolic way (i.e., no energy or nutrients are derived). The enzyme must be induced by a different compound (e.g., *Pseudomonas cepacia* uses toluene-4-monoxygenase, which requires induction by toluene, to destroy trichloroethylene). Furthermore, the degradation pathway involves formation of highly reactive epoxides that can inactivate the enzyme (Timmis et al. Ann. Rev. Microbiol. 48:525-557 (1994)). The GEOS recombination techniques of the invention could be used to generate libraries of genes having mutations to coding sequence enzymes and its regulatory region such that it is produced constitutively, and is less susceptible to epoxide inactivation. In some embodiments of the invention, selection of hosts constitutively producing the enzyme and less susceptible to the epoxides can be accomplished by demanding growth in the presence of increasing concentrations of trichloroethylene in the absence of inducing substances.

c) Polychlorinated Biphenyls (PCBs) and Polycyclic Aromatic Hydrocarbons (PAHs)

PCBs and PAHs are families of structurally related compounds that are major pollutants at many Superfund sites. Bacteria transformed with plasmids encoding enzymes with broader substrate specificity have been used commercially. In nature, no known pathways have been generated in a single host that degrade the larger PAHs or more heavily chlorinated PCBs. Indeed, often the collaboration of anaerobic and aerobic bacteria are required for complete metabolism.

Thus, likely sources for starting material for GEOS recombination include identified genes encoding PAH-degrading catabolic pathways on large (20-100 KB) plasmids (Sanseverino et al. Applied Environ. Micro. 59:1931-1937 (1993); Simon et al. Gene 127:31-37 (1993); Zylstra et al. Annals of the NY Acad. Sci. 721:386-398 (1994)); while biphenyl and PCB-metabolizing enzymes are encoded by chromosomal gene clusters, and in a number of cases have been cloned onto plasmids (Hayase et al. J. Bacteriol. 172: 1160-1164 (1990); Furukawa et al. Gene 98:21-28 (1992); Hofer et al. Gene 144:9-16 (1994)). The materials can be subjected to the techniques discussed above so as to evolve a biodegradative pathway in a single organism.

Substrate specificity in the PCB pathway largely results from enzymes involved in initial dioxygenation reactions, and can be significantly altered by mutations in those enzymes (Erickson et al. Applied Environ. Micro. 59:3858-38662 (1993); Furukawa et al. J. Bact. 175:5224-5232 (1993). Mineralization of PAHs and PCBs requires that the downstream pathway is able to metabolize the products of the initial reaction (Brenner et al. Biodegradation 5:359-377 (1994)). In this case, application of the subject method to the entire pathway with selection for bacteria able to use the PCB or PAH as the sole carbon source can allow production of novel PCB and PAH degrading bacteria.

d) Herbicides

A general method for evolving genes for the catabolism of insoluble herbicides is exemplified as follows for atrazine. Atrazine [2-chloro-4-ethylamino)-6-isopropylamino)-1,3,5-triazine] is a moderately persistent herbicide which is frequently detected in ground and surface water at concentrations exceeding the 3 ppb health advisory level set by the EPA. Atrazine can be slowly metabolized by a *Pseudomonas* species (Mandelbaum et al. Appl. Environ. Micro. 61:1451-1457 (1995)). The enzymes catalyzing the first two steps in atrazine metabolism by *Pseudomonas* are encoded by genes AtzA and AtzB (de Souza et al. Appl. Environ. Micro. 61:3373-3378 (1995)). These genes can be cloned from various species. *E. coli* engineered with these genes convert atrazine to much more soluble metabolites. It is thus possible to screen for enzyme activity by growing bacteria on plates containing atrazine. The herbicide forms an opaque precipitate in the plates, but cells expressing the AtzA and AtzB genes secrete atrazine degrading enzymes, leading to a clear halo around those cells or colonies. Typically, the size of the halo and the rate of its formation can be used to assess the level of activity so that picking colonies with the largest halos allows selection of the more active or highly produced atrazine degrading enzymes. Thus, this pathway can be subjected to GEOS sequence recombination formats described above to optimize the catabolism of atrazine in *E. coli* or another host of choice, including *Pseudomonas*. Screening of host colonies expressing the evolved genes can be done on agar plates containing atrazine to observe halo formation. This is a generally applicable method for screening enzymes that metabolize insoluble compounds to those that are soluble (e.g., polycyclicaromatic hydrocarbons). Additionally, catabolism of atrazine can provide a source of nitrogen for the cell; if no other nitrogen is available, cell growth will be limited by the rate at which the cells can catabolize nitrogen. Cells able to utilize atrazine as a nitrogen source can thus be selected from a background of non-utilizers or poor-utilizers.

e) Heavy Metal Detoxification

Bacteria are used commercially to detoxify arsenate waste generated by the mining of arsenopyrite gold ores. As well as mining effluent, industrial waste water is often contaminated with heavy metals (e.g., those used in the manufacture of electronic components and plastics). Thus, simply to be able to perform other bioremedial functions, microorganisms must be resistant to the levels of heavy metals present, including mercury, arsenate, chromate, cadmium, silver, etc.

A strong selective pressure is the ability to metabolize a toxic compound to one less toxic. Heavy metals are toxic largely by virtue of their ability to denature proteins (Ford et al. Bioextraction and Biodeterioration of Metals, p. 1-23). Detoxification of heavy metal contamination can be effected in a number of ways including changing the solubility or bioavailability of the metal, changing its redox state (e.g. toxic mercuric chloride is detoxified by reduction to the much more volatile elemental mercury) and even by bioaccumulation of the metal by immobilized bacteria or plants. The accumulation of metals to a sufficiently high concentration allows metal to be recycled; smelting burns off the organic part of the organism, leaving behind reusable accumulated metal. Resistances to a number of heavy metals (arsenate, cadmium, cobalt, chromium, copper, mercury, nickel, lead, silver, and zinc) are plasmid encoded in a number of species including *Staphylococcus* and *Pseudomonas* (Silver et al. Environ. Health Perspect. 102:107-113 (1994); Ji et al. J. Ind.

Micro. 14:61-75 (1995)). These genes also confer heavy metal resistance on other species as well (e.g., *E. coli*). The GEOS recombination techniques of the instant invention can be used to increase microbial heavy metal tolerances, as well as to increase the extent to which cells will accumulate heavy metals. For example, the ability of *E. coli* to detoxify arsenate can be improved.

Cyanide is very efficiently used to extract gold from rock containing as little as 0.2 oz per ton. This cyanide can be microbially neutralized and used as a nitrogen source by fungi or bacteria such as *Pseudomonas fluorescens*. A problem with microbial cyanide degradation is the presence of toxic heavy metals in the leachate. GEOS can be used to increase the resistance of bioremedial microorganisms to toxic heavy metals, so that they will be able to survive the levels present in many industrial and Superfund sites. This will allow them to biodegrade organic pollutants including but not limited to aromatic hydrocarbons, halogenated hydrocarbons, and biocides.

f) Microbial Mining

"Bioleaching" is the process by which microbes convert insoluble metal deposits (usually metal sulfides or oxides) into soluble metal sulfates. Bioleaching is commercially important in the mining of arsenopyrite, but has additional potential in the detoxification and recovery of metals and acids from waste dumps. Naturally occurring bacteria capable of bioleaching are reviewed by Rawlings and Silver (Bio/Technology 13:773-778 (1995)). These bacteria are typically divided into groups by their preferred temperatures for growth. The more important *mesophiles* are *Thiobacillus* and *Leptospirillum* species. Moderate thermophiles include *Sulfobacillus* species. Extreme thermophiles include *Sulfolobus* species. Many of these organisms are difficult to grow in commercial industrial settings, making their catabolic abilities attractive candidates for transfer to and optimization in other organisms such as *Pseudomonas, Rhodococcus, T. ferrooxidans* or *E. coli*. Genetic systems are available for at least one strain of *T. ferrooxidans*, allowing the manipulation of its genetic material on plasmids.

The GEOS recombination methods described above can be used to optimize the catalytic abilities in native hosts or heterologous hosts for evolved bioleaching genes or pathways, such as the ability to convert metals from insoluble to soluble salts. In addition, leach rates of particular ores can be improved as a result of, for example, increased resistance to toxic compounds in the ore concentrate, increased specificity for certain substrates, ability to use different substrates as nutrient sources, and so on.

g) Oil Desulfurization

The presence of sulfur in fossil fuels has been correlated with corrosion of pipelines, pumping, and refining equipment, and with the premature breakdown of combustion engines. Sulfur also poisons many catalysts used in the refining of fossil fuels. The atmospheric emission of sulfur combustion products is known as acid rain.

Microbial desulfurization is an appealing bioremediation application. Several bacteria have been reported that are capable of catabolizing dibenzothiophene (DBT), which is the representative compound of the class of sulfur compounds found in fossil fuels. U.S. Pat. No. 5,356,801, for example, discloses the cloning of a DNA molecule from *Rhodococcus rhodochrous* capable of biocatalyzing the desulfurization of oil. Denome et al. (Gene 175:6890-6901 (1995)) disclose the cloning of a 9.8 kb DNA fragment from *Pseudomonas* encoding the upper naphthalene catabolizing pathway which also degrades dibenzothiophene. Other genes have been identified that perform similar functions (such as disclosed in U.S. Pat. No. 5,356,801).

The activity of these enzymes is currently too low to be commercially viable, but the pathway could be increased in efficiency using the GEOS recombination techniques of the invention. The desired property of the genes of interest is their ability to desulfurize dibenzothiophene. In some embodiments of the invention, selection is preferably accomplished by coupling this pathway to one providing a nutrient to the bacteria. Thus, for example, desulfurization of dibenzothiophene results in formation of hydroxybiphenyl. This is a substrate for the biphenyl-catabolizing pathway which provides carbon and energy. Selection would thus be done by "shuffling" the dibenzothiophene genes and transforming them into a host containing the biphenyl-catabolizing pathway. Increased dibenzothiophene desulfurization will result in increased nutrient availability and increased growth rate.

h) Organo-Nitro Compounds

Organo-nitro compounds are used as explosives, dyes, drugs, polymers and antimicrobial agents. Biodegradation of these compounds occurs usually by way of reduction of the nitrate group, catalyzed by nitroreductases, a family of broadly-specific enzymes. Partial reduction of organo-nitro compounds often results in the formation of a compound more toxic than the original (Hassan et al. 1979 Arch Bioch Biop. 196:385-395). GEOS recombination of nitroreductases can produce enzymes that are more specific, and able to more completely reduce (and thus detoxify) their target compounds (examples of which include but are not limited to nitrotoluenes and nitrobenzenes). Nitro-reductases can be isolated from bacteria isolated from explosive-contaminated soils, such as *Morganella morganii* and *Enterobacter cloacae* (Bryant et. al., 1991. J. Biol Chem. 266:4126-4130). A preferred selection method is to look for increased resistance to the organo-nitro compound of interest, since that will indicate that the enzyme is also able to reduce any toxic partial reduction products of the original compound.

vii) Use of Alternative Substrates for Chemical Synthesis

Metabolic engineering can be used to alter microorganisms that produce industrially useful chemicals, so that they will grow using alternate and more abundant sources of nutrients, including human-produced industrial wastes. This typically involves providing both a transport system to get the alternative substrate into the engineered cells and catabolic enzymes from the natural host organisms to the engineered cells. In some instances, enzymes can be secreted into the medium by engineered cells to degrade the alternate substrate into a form that can more readily be taken up by the engineered cells; in other instances, a batch of engineered cells can be grown on one preferred substrate, then lysed to liberate hydrolytic enzymes for the alternate substrate into the medium, while a second inoculum of the same engineered host or a second host is added to utilize the hydrolyzate.

The starting materials for the subject recombination method will typically be genes for utilization of a substrate or its transport. Examples of nutrient sources of interest include but are not limited to lactose, whey, galactose, mannitol, xylan, cellobiose, cellulose and sucrose, thus allowing cheaper production of compounds including but not limited to ethanol, tryptophan, rhamnolipid surfactants, xanthan gum, and polyhydroxylalkanoate. For a review of such substrates as desired target substances, see Cameron et al. (Appl. Biochem. Biotechnol. 38:105-140 (1993)).

The GEOS recombination methods described herein can be used to optimize the ability of native hosts or heterologous hosts to utilize a substrate of interest, to evolve more efficient transport systems, to increase or alter specificity for certain substrates, and so on.

viii) Modification of Cell Properties.

Although not strictly examples of manipulation of intermediary metabolism, GEOS recombination techniques can be used to improve or alter other aspects of cell properties, from growth rate to ability to secrete certain desired compounds to ability to tolerate increased temperature or other environmental stresses. Some examples of traits engineered by traditional methods include expression of heterologous proteins in bacteria, yeast, and other eukaryotic cells, antibiotic resistance, and phage resistance. Any of these traits is advantageously evolved by the GEOS recombination techniques of the instant invention. Examples include replacement of one nutrient uptake system (e.g. ammonia in *Methylophilus methylotrophus*) with another that is more energy efficient; expression of haemoglobin to improve growth under conditions of limiting oxygen; redirection of toxic metabolic end products to less toxic compounds; expression of genes conferring tolerance to salt, drought and toxic compounds and resistance to pathogens, antibiotics and bacteriophage, reviewed in Cameron et. al. Appl Biochem Biotechnol, 38:105-140 (1993).

The heterologous genes encoding these functions all have the potential for further optimization in their new hosts by existing GEOS recombination technology. Since these functions increase cell growth rates under the desired growth conditions, optimization of the genes by "evolution" can simply involve "shuffling" the DNA and selecting the recombinants that grow faster with limiting oxygen, higher toxic compound concentration or whatever restrictive condition is being overcome.

Cultured mammalian cells also require essential amino acids to be present in the growth medium. This requirement could also be circumvented by expression of heterologous metabolic pathways that synthesize these amino acids (Rees et al. Biotechnology 8:629-633 (1990). GEOS recombination would provide a mechanism for optimizing the expression of these genes in mammalian cells. Once again, a preferred election would be for cells that can grow in the absence of added amino acids.

Yet another candidate for improvement through the techniques of the invention is symbiotic nitrogen fixation. Genes involved in nodulation (nod, ndv), nitrogen reduction (nif, fix), host range determination (nod, hsp), bacteriocin production (tfx), surface polysaccharide synthesis (exo) and energy utilization (dct, hup) which have been identified (Paau, Biotech. Adv. 9:173-184 (1991)).

The main function of GEOS recombination in this case is in improving the survival of strains that are already known to be better nitrogen fixers. These strains tend to be less good at competing with strains already present in the environment, even though they are better at nitrogen fixation. Targets for GEOS recombination such as nodulation and host range determination genes can be modified and selected for by their ability to grow on the new host. Similarly any bacteriocin or energy utilization genes that will improve the competitiveness of the strain will also result in greater growth rates. Selection can simply be performed by subjecting the target genes to GEOS recombination and forcing the inoculant to compete with wild type nitrogen fixing bacteria. The better the nitrogen fixing bacteria grow in the new host, the more copies of their recombined genes will be present for the next round of recombination. This growth rate differentiating selection is described herein in detail.

ix) Biodetectors/Biosensors

Bioluminescence or fluorescence genes can be used as reporters by fusing them to specific regulatory genes (Cameron et. al. Appl Biochem Biotechnol, 38:105-140 (1993)). A specific example is one in which the luciferase genes luxCD-ABE of *Vibrio fischeri* were fused to the regulatory region of the isopropylbenzene catabolism operon from *Pseudomonas putida* RE204. Transformation of this fusion construct into *E. coli* resulted in a strain which produced light in response to a variety of hydrophobic compound such as substituted benzenes, chlorinated solvents and naphthalene (Selifonova et. al., Appl Environ Microbiol 62:778-783 (1996)). This type of construct is useful for the detection of pollutant levels, and has the added benefit of only measuring those pollutants that are bioavailable (and therefore potentially toxic). Other signal molecules such as jellyfish green fluorescent protein could also be fused to genetic regulatory regions that respond to chemicals in the environment. This should allow a variety of molecules to be detected by their ability to induce expression of a protein or proteins which result in light, fluorescence or some other easily detected signal.

GEOS recombination can be used in several ways to modify this type of biodetection system. It can be used to increase the amplitude of the response, for example by increasing the fluorescence of the green fluorescent protein. GEOS recombination could also be used to increase induced expression levels or catalytic activities of other signal-generating systems, for example of the *luciferase* genes.

GEOS recombination can also be used to alter the specificity of biosensors. The regulatory region, and transcriptional activators that interact with this region and with the chemicals that induce transcription can also be shuffled. This should generate regulatory systems in which transcription is activated by analogues of the normal inducer, so that biodetectors for different chemicals can be developed. In this case, selection would be for constructs that are activated by the (new) specific chemical to be detected. Screening could be done simply with fluorescence (or light) activated cell sorting, since the desired improvement is in light production.

In addition to detection of environmental pollutants, biosensors can be developed that will respond to any chemical for which there are receptors, or for which receptors can be evolved by GEOS recombination, such as hormones, growth factors, metals and drugs. These receptors may be intracellular and direct activators of transcription, or they may be membrane bound receptors that activate transcription of the signal indirectly, for example by a phosphorylation cascade. They may also not act on transcription at all, but may produce a signal by some post-transcriptional modification of a component of the signal generating pathway. These receptors may also be generated by fusing domains responsible for binding different ligands with different signaling domains. Again, GEOS recombination can be used to increase the amplitude of the signal generated to optimize expression and functioning of chimeric receptors, and to alter the specificity of the chemicals detected by the receptor.

IV. EXAMPLES

The following examples are by way of illustration and are not intended to limit the claims. Persons of skill will readily recognize that the protocols of the examples can be modified in numerous non-critical ways.

Simultaneous Assembly of a Viable Plasmid Vector

To demonstrate the simultaneous assembly of multiple nucleic acid components having unique, non-palindromic terminal sequences, to produce a viable plasmid vector, three nucleic acid components are used. The first nucleic acid component is a gene coding for green fluorescent protein, 0.7 Kb in length, the second one is a 0.6 Kb molecule coding for terminator sequences and a histidine tag, and the third one is a 2.5 Kb molecule coding for the lac promoter, an ampicillin resistance gene, and an origin of replication.

1. Synthesis of the Nucleic Acid Components

The nucleic acid components used in the present example are synthesized by PCR amplification. The PCR reactions are performed in varying volumes (in general, 10-100 microliters) containing a 50 mM KCl, 10 mM Tris-HCI (pH 8.4), 1.5 mM $MgCl_2$ buffer and 0.2 mM of each dNTP, 1.25 units of taq DNA polymerase, $10^{-5}$ M template molecules, and 20 pmol of each primer. The primers used contain uracil residues at specific locations in order to generate 3' terminal sequences as described in U.S. Pat. No. 5,137,814. The PCR reaction is carried out using a thermal cycling instrument, where there is an initial denaturation phase of 95° C. for 5 minutes, followed by multiple cycles (20-40 cycles) of a denaturation step at 94° C., an annealing step at 37-65° C. and an extension step at 72° C. The resulting PCR products are analyzed by gel electrophoresis to determine size and purity.

2. Generation of Terminal Sequences

Following PCR amplification and purification of the correct size fragments, the PCR products (approximately 100-200 ng) are dissolved in 10 microliters of the UDG reaction buffer (25 mM Tris-HCI (pH 7.8), 10 mM $Mg_2Cl$, 4 mM beta-mercaptoethanol, 0.4 mM ATP). Single-stranded 3' Terminal sequences are made by treatment of the PCR product with 1-2 units of uracil DNA glycosidase (UDG) for 10 minutes at 37° C. The enzyme is inactivated and reaction is terminated by heating the sample at 65° C. for 10 minutes.

3. Assembly and Ligation of the Nucleic Acid Components

To assemble the vector the individual purified nucleic acid components are mixed in equimolar amounts (approximately 20-200 ng total in 20 microliters) in the UDG treatment buffer and heated to 65° C., followed by gradually cooling down to room temperature (25° C.), to permit efficient annealing of the complementary ends of the nucleic acid components. The reaction mixture may optionally be treated with T4 DNA ligase at 14° C. overnight to ligate the nucleic acid components or used directly to transform competent bacterial hosts.

4. Transformation

A 10 μl aliquot of the assembled vector is added to 100 μl of competent *E. coli* cells (DH5α), transformed following the manufacturers recommendations, and plated on LB plates containing ampicillin and IPTG.

5. Analysis of the Vector Construct

Isolated fluorescent colonies are selected and pure DNA plasmid prepared using a mini-prep. Correct assembly of the vector construct is determined using standard molecular biological methods, such as restriction enzyme digestion and agarose gel electrophoresis.

All of the above-cited references and publications are hereby incorporated by reference.

V. Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of obtaining a nucleic acid multicomponent construct having a desirable functionality comprising:
   (a) providing a collection of nucleic acid components, each component comprising at least one genetic element having a known functionality and at least one single-stranded 5' or 3' terminal sequence, and
   (b) selecting at least three nucleic acid components, wherein a first nucleic acid component is selected from a category of first nucleic acid components having a common biological utility or functionality, a second nucleic acid component is selected from a category of second nucleic acid components having a common biological utility or functionality, and a third nucleic acid component selected from a category of third nucleic acid component having a common biological utility or functionality, wherein the biological utility or functionality of each of the first, second and third categories is different from the other categories, and
   (c) assembling said at least three nucleic acid components by hybridization of the terminal sequence to either a terminal sequence in another of said at least three nucleic acid components, thereby producing a nucleic acid multicomponent construct with desired functionality.

2. The method of claim 1, wherein one or more of the nucleic acid components provide a single functionality.

3. The method of claim 1, wherein one or more of the nucleic acid components provide multiple functionalities.

4. The method of claim 1, wherein at least one of the single stranded terminal sequences are non-palindromic.

5. The method of claim 1, wherein the nucleic acid components are incubated simultaneously.

6. The method of claim 1, wherein the nucleic acid components are incubated in a step-wise fashion.

7. The method of claim 1, wherein the nucleic acid components are linked directly via annealing of 5' complementary terminal sequences.

8. The method of claim 1, wherein the nucleic acid components are linked directly via annealing of 3' complementary terminal sequences.

9. The method of claim 1, wherein the nucleic acid components are linked indirectly via a linking nucleic acid molecule, the linking nucleic acid molecule comprising an oligonucleotide.

10. The method of claim 1, wherein the nucleic acid components are linked indirectly via a linking nucleic acid molecule, the linking nucleic acid molecule comprising an adaptor molecule, the adaptor molecule having terminal sequences that are complementary with 5' or 3' terminal sequences in separate nucleic acid components.

11. The method of claim 1, wherein the nucleic acid component encodes a biological functionality selected from the group consisting of origin of replication, selectable marker, transcriptional regulatory element, structural gene or fragment thereof, transcription termination signal, translational regulatory sequence, regulators of mRNA stability, cellular localization signal, recombination elements, mutagenized genes, protein domain encoded regions, synthetic multiple cloning sites, unique restriction enzyme or DNA cleavage sites, site for covalent or non covalent attachment of a biological or chemical molecule, and a protein coding sequence.

12. The method of claim 1, wherein each of the first, second, and third nucleic acid components is appropriately phosphorylated for ligation.

13. The method of claim 11, wherein the origin of replication is selected from the group consisting of: a bacterial origin of replication, a viral origin of replication, a phage origin of replication, a eukaryotic origin of replication, a yeast origin of replication, and a mammalian origin of replication.

14. The method of claim 11, wherein the selectable marker gene is selected from the group consisting of: an antibiotic resistance selectable marker, a drug resistance selectable marker, and a mutagenic resistance selectable marker.

15. The method of claim 11, wherein the protein coding sequence is selected from the group consisting of: a cDNA, a structural gene, a fragment of a structural gene, a mutagenized structural gene, and a mutagenized fragment of a structural gene.

16. The method of claim 11, wherein the DNA cleavage site is part of a multiple cloning site.

17. The method of claim 1, wherein at least two of said at least three nucleic acid components are supplied as at least three different nucleic acid species, each of which provides an alternative form of the common biological utility or functionality of the nucleic acid component.

18. The method of claim 1, wherein the nucleic acid component is covalently or non-covalently modified.

19. The method of claim 1, wherein the nucleic acid is selected from the group consisting of a vector, a gene, or a gene fragment.

* * * * *